(12) United States Patent
Iscoe et al.

(10) Patent No.: US 9,949,697 B2
(45) Date of Patent: Apr. 24, 2018

(54) IMAGING A BODY

(71) Applicant: MyFiziq Limited, South Perth (AU)

(72) Inventors: Katherine Iscoe, Subiaco (AU); Vlado Bosanac, Subiaco (AU); Amar El-Sallam, Subiaco (AU)

(73) Assignee: MyFiziq Limited, South Perth (AU)

( * ) Notice: Subject to any disclaimer, the term of this patent is extended or adjusted under 35 U.S.C. 154(b) by 0 days.

(21) Appl. No.: 15/612,441

(22) Filed: Jun. 2, 2017

(65) Prior Publication Data

US 2017/0273639 A1  Sep. 28, 2017

Related U.S. Application Data

(63) Continuation of application No. PCT/AU2015/000736, filed on Dec. 4, 2015.

(30) Foreign Application Priority Data

Dec. 5, 2014  (AU) ................................ 2014904940

(51) Int. Cl.
*G06T 13/40* (2011.01)
*A61B 5/00* (2006.01)
(Continued)

(52) U.S. Cl.
CPC ............ *A61B 5/744* (2013.01); *A61B 5/0064* (2013.01); *A61B 5/0075* (2013.01);
(Continued)

(58) Field of Classification Search
USPC .......................................... 345/419
See application file for complete search history.

(56) References Cited

U.S. PATENT DOCUMENTS

| 5,581,276 A | 12/1996 | Cipolla et al. |
| 6,980,671 B2 * | 12/2005 | Liu .................... G06K 9/00201 |
| | | 375/E7.084 |

(Continued)

FOREIGN PATENT DOCUMENTS

| EP | 587138 A2 | 3/1994 |
| EP | 2210235 B1 | 2/2011 |

(Continued)

OTHER PUBLICATIONS

Liu et al. "3D real human reconstruction via multiple low-cost depth cameras". Publishe Oct. 2014.*

(Continued)

*Primary Examiner* — Kimbinh T Nguyen
(74) *Attorney, Agent, or Firm* — Marshall, Gerstein & Borun LLP

(57) ABSTRACT

There is disclosed a device for imaging a body. In one arrangement, the device comprises a controller, storage storing electronic program instructions for controlling the controller, a display for displaying a user interface, and an input means. In one form, the controller is operable, under control of the electronic program instructions, to receive input via the input means, where the input comprises a first representation of the body, to process the first representation, to generate a second representation of the body on the basis of processing of the first representation, and to display the generated second representation via the display.

26 Claims, 3 Drawing Sheets

(2 of 3 Drawing Sheet(s) Filed in Color)

(51) Int. Cl.

| | |
|---|---|
| G06F 19/00 | (2018.01) |
| G06N 99/00 | (2010.01) |
| G06N 5/04 | (2006.01) |
| G06F 3/16 | (2006.01) |
| G06F 3/0481 | (2013.01) |
| G06T 7/33 | (2017.01) |
| G06T 7/194 | (2017.01) |
| A61B 5/107 | (2006.01) |
| A61B 5/11 | (2006.01) |
| G06T 17/20 | (2006.01) |

(52) U.S. Cl.
CPC .......... *A61B 5/0077* (2013.01); *A61B 5/1072* (2013.01); *A61B 5/1073* (2013.01); *A61B 5/1079* (2013.01); *A61B 5/1128* (2013.01); *A61B 5/7475* (2013.01); *G06F 3/04815* (2013.01); *G06F 3/167* (2013.01); *G06F 19/321* (2013.01); *G06F 19/3437* (2013.01); *G06F 19/3481* (2013.01); *G06N 5/04* (2013.01); *G06N 99/005* (2013.01); *G06T 7/194* (2017.01); *G06T 7/33* (2017.01); *G06T 13/40* (2013.01); *G16H 50/50* (2018.01); *A61B 2562/028* (2013.01); *A61B 2562/0219* (2013.01); *G06F 19/3406* (2013.01); *G06T 17/20* (2013.01); *G06T 2200/24* (2013.01); *G06T 2207/10028* (2013.01); *G06T 2207/30196* (2013.01); *G06T 2210/56* (2013.01); *G16H 40/63* (2018.01)

(56) References Cited

U.S. PATENT DOCUMENTS

| | | | |
|---|---|---|---|
| 7,577,280 | B2 | 8/2009 | Guittet et al. |
| 7,970,205 | B2 | 6/2011 | Iwasaki et al. |
| 8,374,671 | B2 | 2/2013 | Barnes |
| 8,417,021 | B2 | 4/2013 | Cipolla et al. |
| 8,437,549 | B2 | 5/2013 | Iwasaki et al. |
| 8,451,322 | B2 | 5/2013 | Hernandez et al. |
| 8,842,906 | B2 * | 9/2014 | Watson ............ G06T 7/75 382/107 |
| 2009/0073259 | A1 * | 3/2009 | Hernandez ......... G06T 7/586 348/48 |
| 2009/0124866 | A1 * | 5/2009 | Guillama ........ G06F 19/3437 600/300 |
| 2010/0111370 | A1 * | 5/2010 | Black ............. G06K 9/00369 382/111 |
| 2010/0239123 | A1 | 9/2010 | Funayama et al. |
| 2012/0082381 | A1 | 4/2012 | Maki et al. |
| 2012/0106794 | A1 * | 5/2012 | Iwasaki ............. G06T 7/215 382/103 |
| 2012/0271143 | A1 | 10/2012 | Aragones et al. |
| 2012/0287247 | A1 | 11/2012 | Stenger et al. |
| 2013/0325493 | A1 | 12/2013 | Wong et al. |
| 2013/0336550 | A1 * | 12/2013 | Kapur ............. G06K 9/00369 382/128 |
| 2014/0100464 | A1 * | 4/2014 | Kaleal ............... A61B 5/0205 600/508 |

FOREIGN PATENT DOCUMENTS

| | | |
|---|---|---|
| GB | 2452944 B | 8/2010 |
| GB | 2464453 B | 9/2010 |
| JP | H11-192214 A | 7/1999 |
| JP | 2002150292 A | 5/2002 |
| WO | WO-2004/047004 A2 | 6/2004 |
| WO | WO-2007/042844 A2 | 4/2007 |
| WO | WO-2007/096652 A2 | 8/2007 |
| WO | WO-2008/065319 A1 | 6/2008 |
| WO | WO-2009/047366 A2 | 4/2009 |
| WO | WO-2009/112790 A1 | 9/2009 |
| WO | WO-2011/113444 A1 | 9/2011 |
| WO | WO-2011/154165 A1 | 12/2011 |

OTHER PUBLICATIONS

Zhang et al. "Quality Dynamic Human Body Modeling Using a Single Low-cost Depth camera"; published 2014.*
International Search Report and Written Opinion in International Application No. PCT/AU2015/000736 dated Mar. 30, 2016, 12 pages.
International Preliminary Report on Patentability in International Application No. PCT/AU2015/000736 dated Jan. 9, 2017, 140 pages.
El-Sallam et al., "Towards a Fully Automatic Markerless Motion Analysis System for the Estimation of Body Joint Kinematics with Application to Sport Analysis", International Joint Conference on Computer Vision, Imaging and Computer Graphics Theory and Applications, GRAPP, 2015, 12 pages.
Badrinarayanan et al., "Semi-Supervised Video Segmentation Using Tree Structured Graphical Models", IEEE Trans. Pattern Analysis and Machine Intelligence, 35(11), 2013, 14 pages.
Shotton et al., "Semantic Texton Forests for Image Categorization and Segmentation", Decision Forests for Computer Vision and Medical Image Analysis, Springer, 2013, 8 pages.
Kim et al., "Multiple Classifier Boosting and Tree-Structured Classifiers", Machine Learning for Computer Vision, Springer, 2013, pp. 163-196.
Pham et al., "Scale-Invariant Vote-Based 3D Recognition and Registration From Point Clouds", Machine Learning for Computer Vision, Springer, 2013, pp. 137-162.
Rossi et al., "Body Segment Inertial Parameters of Elite Swimmers Using DXA and Indirect Methods", Journal of Sports Science and Medicine 12, 2013, pp. 761-775.
Shah et al., "A Novel Local Surface Description for Automatic 3D Object Recognition in Low Resolution Cluttered Scenes", International Conference on Computer Vision (ICCV) Workshop, 2013, pp. 638-643.
Shah et al., "3D-DIV: A Novel Local Surface Descriptor for Feature Matching and Pairwise Range Image Registration", IEEE International Conference on Image Processing (ICIP) 2013, pp. 2934-2938.
Sedai et al., "3D Human Pose Tracking Using Gaussian Process Regression and Particle Filter Applied to Gait Analysis of Parkinson's Disease Patients", The 8th IEEE Conference on Industrial Electronics and Applications (ICIEA) 2013, pp. 1636-1642.
Rossi et al., "Trunk Inertial Parameters of Elite Male and Female Swimmers: Analysis Using DXA and Estimation of Errors from Indirect Estimation Methods", XXIV Congress of the International Society of Biomechanics (ISB) 2013, Brazil, 2 pages.
El-Sallam et al., "A Low Cost Visual Hull Based Markerless System for the Optimization of Athletic Techniques in Outdoor Environments", 8th International Joint Conference on Computer Vision, Imaging and Computer Graphics Theory and Applications, GRAPP, 2013, pp. 49-59.
Rossi et al., "A Novel Approach to Calculate Body Segments Inertial Parameters From DXA and 3D Scanners Data", 4th International Conference on Computational Methods (ICCM), Australia, 2012, 9 pages.
Hayat et al., "Evaluation of Spatiotemporal Detectors and Descriptors for Facial Expression Recognition", 5th International Conference on Human System Interactions, 2012, pp. 43-47.
Chen et al., "A Practical System for Modelling Body Shapes From Single View Measurements", http://mi.eng.cam.ac.uk/cipolla/publications/inproceedings/2011-BMVC-Metail.pdf, 2011, 11 pages.
Stenger et al., "A Vision-Based Remote Control", Detection, Recognition and Reconstruction, Springer, 2010, 29 pages.
Zhou et al., "Parametric Reshaping of Human Bodies in Images", ACM Transactions on Graphics, vol. 29, No. 4, Article 126, 2010, pp. 1-126:10.
Robertson et al., "Structure From Motion", Practical Image Processing and Computer Vision, 2009, 49 pages.
El-Sallam et al., "A High Resolution Color Image Restoration Algorithm for Thin TOMBO Imaging Systems", Sensors, 9, 2009, pp. 4649-4668.
El-Sallam et al., "Spectral-Based Blind Image Restoration Method for Thin TOMBO Imagers", Sensors, 8, 2008, pp. 6108-6124.

(56) References Cited

OTHER PUBLICATIONS

Arandjelovic et al., "Achieving Illumination Invariance Using Image Filters", Face Recognition, Advanced Robotic Systems, I-Tech, Vienna, 2007, 18 pages.
Arandjelovic et al., "Towards Person Authentication by Fusing Visual and Thermal Face Biometrics", Face Biometrics for Personal Identification, Springer, 2007, 19 pages.
Cipolla et al., "Template-Based Hand Detection and Tracking", Advanced Studies in Biometrics, Springer, 2005, pp. 114-125.
Cipolla et al., "Visual Robot Guidance From Uncalibrated Stereo", Realtime Computer Vision, Cambridge University Press, 1994, 19 pages.
Williams, "Virtual Tape Measure Removes the Guesswork From Online Clothes Shopping", http://www.gizmag.com/virtual-tape-measure-online/25130/, retrieved from the internet on Jun. 23, 2017, 2 pages.
Neophytou et al., "ShapeMate: A Virtual Tape Measure". http://www.academia.edu/4419724/ShapeMate_A_virtual_tape_measure, retrieved from the internet on Jun. 23, 2017, 4 pages.
Investigator: P. Delamore, "Body Shape Recognition for Online Fashion", Grant Application, EP/I032169/1, http://gow.epsrc.ac.uk/NGBOViewGrant.aspx?GrantRef-EP/I032169/1, retrieved from the internet on May 30, 2017, 2 pages.
Investigator: A. Hilton, "Body Shape Recognition for Online Fashion", Grant Application, EP/I031936/1, http://gow.epsrc.ac.uk/NGBOViewGrant.aspx?GrantRef-EP/I031936/1, retrieved from the internet on May 30, 2017, 2 pages.
Body Volume, Revolutionary Measurement for Healthcare, Wellness and Fitness, www.bodyvolume.com, retrieved from the internet on Jun. 23, 2017, 1 page.
Elaiwat et al., "A Curvelet-based Approach for Textured 3D Face Recognition", Pattern Recognition, 48, 2015, pp. 1235-1246.
Elaiwat et al., "3-D Face Recognition using Curvelet Local Features", IEEE Signal Processing Letters, vol. 21, No. 2, Feb. 2014, pp. 172-175.
Lei et al., "An Efficient 3D Face Recognition Approach Based on the Fusion of Novel Local Low-level Features", Pattern Recognition 46, 2013, pp. 24-37.
El-Sallam et al., "Human Body Pose Estimation From Still Images and Video Frames", ICIAR, Part I, LNCS 6111, 2010, pp. 176-188.
Zhang et al., "Quality Dynamic Human Body Modeling Using a Single Low-cost Depth Camera", IEEE Conference on Computer Vision and Pattern Recognition, 2014, pp. 676-683.
Alderson et al., "Multi-source Databases, Machine Learning and Markerless Motion Capture: Why Applied Sports Biomechanics Needs Big Data", ISB Congress, Glasgow U.K., 2015, 2 pages.
Lum et al., "Achilles Tendon Moment Arm Geometry in Typically Developing Children", ISB Congress, Glasgow U.K., 2015, 2 pages.

El-Sallam et al., "A Low Cost 3D Markerless System for the Reconstruction of Athletic Techniques", IEEE Workshop on the Applications of Computer Vision, WACV, 2013, pp. 222-229.
Hayat et al., "Clustering of Video-Patches on Grassmannian Manifold for Facial Expression Recognition From 3D Videos", IEEE Workshop on the Applications of Computer Vision, WACV, 2013, pp. 83-88.
Hayat et al., "Fully Automatic Face Recognition From 3D Videos", 21st International Conference on Pattern Recognition ICPR, Nov. 11-15, 2012, pp. 1415-1418.
El-Sallam et al., "Robust Pose Invariant Shape-based Hand Recognition", In Proc. of the IEEE ICIEA Conference, 2011, pp. 281-286.
El-Sallam et al., "Restoration of a High Resolution Image From Multiple Blurred, Low Resolution and Noisy Images", Proceedings of the 2008 IEEE, CIBEC'08, Dec. 2008, 6 pages.
Cipolla et al., "Shape From Profiles", Images and Artefacts of the Ancient World, May 2005, pp. 125-130.
Drummond et al., "Towards Artificial Action: Teaching by Showing", Human and Machine Perception 3: Thinking, Deciding, and Acting, Kluwer Academic Publishers, 2002, pp. 225-236.
R. Cipolla, "Active Visual Inference of Surface Shape", Lecture Notes in Computer Science, Springer-Verlag Heidelberg, 1996, 203 pages.
Cipolla et al., "The Structure and Motion of Surfaces", Dynamical Systems, Control, Coding, Computer Vision, Birkhauser, Basel, Switzerland, 1999, pp. 369-391.
Sato et al., "Quasi-Invariant Parameterisations and Their Applications in Computer Vision", Shape, Contour and Grouping in Computer Vision, Springer-Verlag, Heidelberg, Germany, 1999, pp. 72-92.
Cipolla et al., "A Human-robot Interface Using Pointing with Uncalibrated Stereo Vision", Computer Vision for Human-Machine Interaction, Cambridge University Press, 1998, pp. 97-110.
Gee et al., "Tracking Faces", Computer Vision for Human-Machine Interaction, Cambridge University Press, 1998, pp. 113-122.
Blake et al., "Visual Exploration of Free-space", Active Vision, MIT Press 1992, pp. 175-188.
Cipolla et al., "Motion Planning Using Image Divergence and Deformation", Active Vision, MIT Press 1992, pp. 189-201.
Lawn et al., "Using Uncertainty Estimates to Improve Epipolar Constraint Combination", Segmentation to Interpretation and Back: Mathematical Methods in Computer Vision, Springer-Verlag, 2000.
R. Cipolla, "Image Sequence Analysis of Human Motion", University of Electro-communications, Tokyo, Japan, Master's Thesis (M.Eng), Feb. 1988.
R. Cipolla, "PRF staggering in optimum radar signal processors for moving target detection", University of Pennsylvania, USA, Master's Thesis (M.S.E.), Sep. 1985.
Office Action in Japanese Patent Application No. JP 2017-527800, dated Feb. 6, 2018.

* cited by examiner

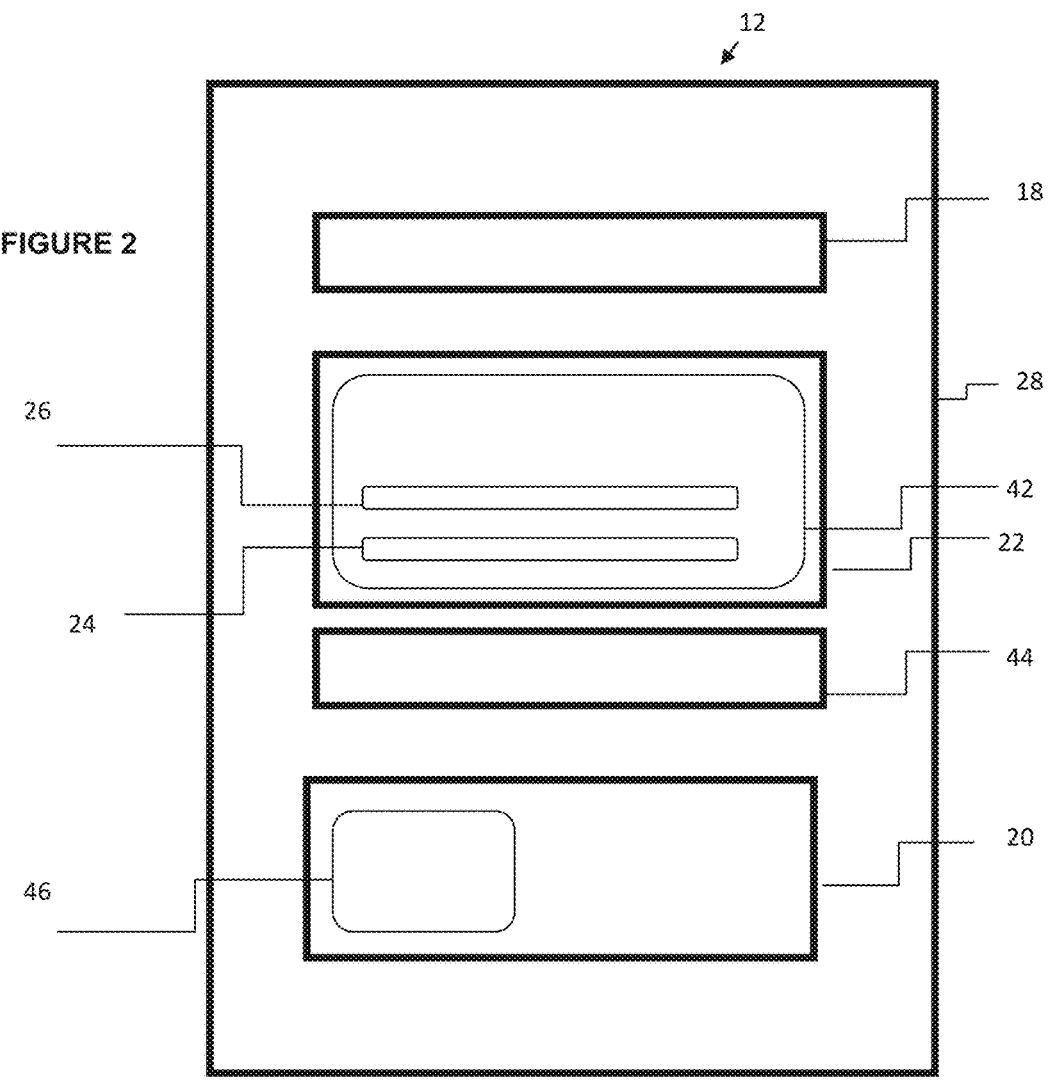
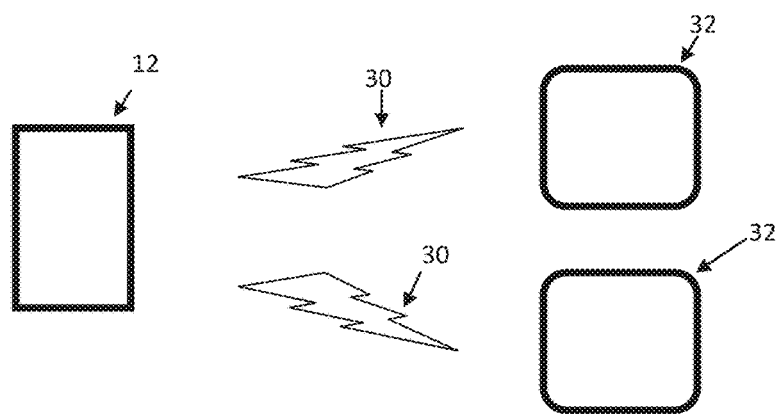

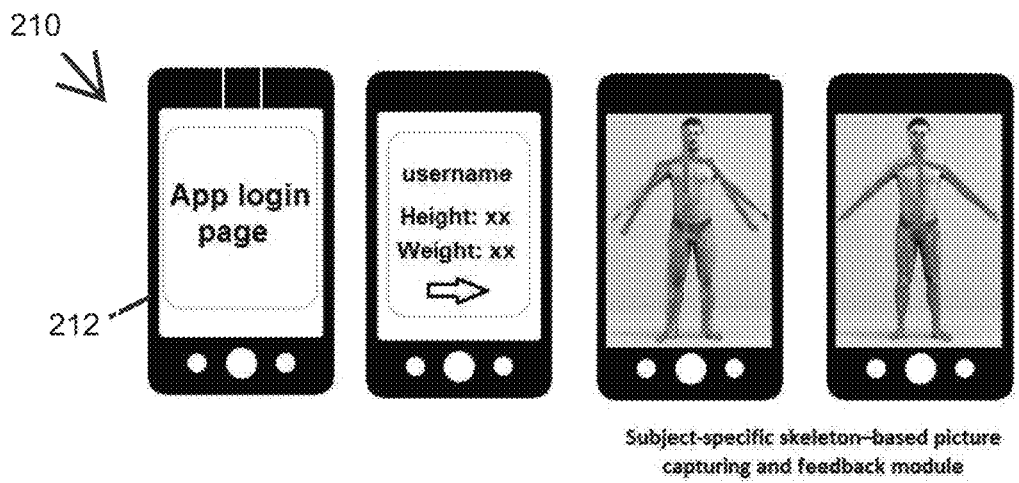

Figure 4: A guiding user-specific skeleton is generated for the user to follow and align their body. Audio feedback will also help the user to capture the optimal pose needed.

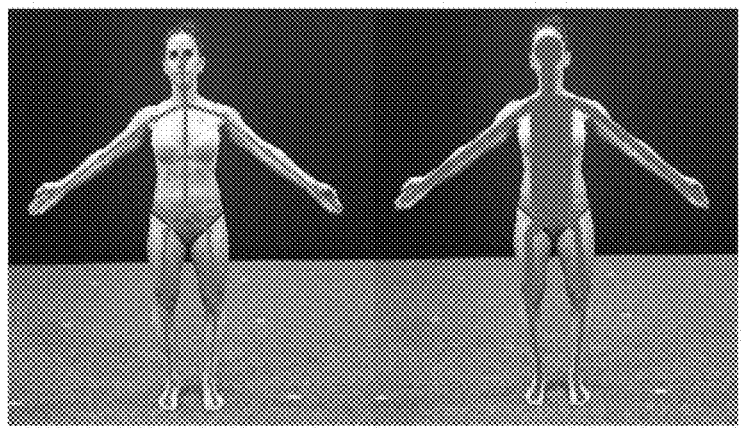

Figure 5: labeling the highly likely user body in an image.
Image pixels aligned to the skeleton are expanded (dilated) according to the bone name. A thicker dilation kernel is used for e.g pixels along the back bone.

IMAGING A BODY

CROSS-REFERENCE TO RELATED APPLICATIONS

This application is a continuation of Application No. PCT/AU2015/000736, filed on Dec. 4, 2015. This application claims the benefit of, and priority to, Australian Provisional Patent Application No. 2014904940, entitled "Imaging a Body" and filed on Dec. 5, 2014. Each of the above-listed applications is hereby incorporated herein by reference in its entirety.

FIELD OF THE INVENTION

The present invention relates generally to imaging a body.

Although the present invention will be described with particular reference to imaging a human body to facilitate achievement of an objective comprising a personal fitness goal, it will be appreciated that it may be used in respect of bodies of other things, and for additional and/or alternative purposes.

BACKGROUND ART

Human obesity has been identified as a global epidemic. According to the publication of the World Health Organisation 2008: Global Burden of Disease Study 2013, *The Lancet*, the number of people classified as overweight increased from an estimated number of 857 million in 1980, to 2.1 billion in 2013, with 4 billion people being predicted as being overweight by 2030.

This has an economic cost. For example, in the United Kingdom, in 2007 it was estimated that 42% of men and 32% of women were overweight having an estimated cost to the economy of US$26 billion, in the United States of America, in 2010 it was estimated that 74% of men and 64% of women were overweight having an estimated cost to the economy of US$147 billion, and in Australia, in 2012 it was estimated that 42% of men and 28% of women were overweight having an estimated cost to the economy of US$53 billion. [National Health and Medical Research Council (NHMRC), Australian Heart Foundation; Centre for Disease Control (CDC); National Health and Nutrition Examination Survey (NHANES); The Health and Social Care Information Centre (HSCIC).]

Furthermore, it has been reported that: over half of Australians (55.7%) and Americans (51%) are trying to lose weight; 45% of women and 23% of men in the healthy weight range think that they are overweight; approximately 91% of women are unhappy with their bodies; and the increase in obesity is mainly occurring in 20 to 40 year olds. [Jeffery R W, Sherwood N E, Brelje K, et al. Mail and phone interventions for weight loss in a managed-care setting: Weigh-To-Be one-year outcomes. Int J Obes Related Metab Disord. 2003; 27(12):1584-1592; Linde J A, Jeffery R W, French S A, Pronk N P, Boyle R G. Self-weighing in weight gain prevention and weight loss trials. Ann Behav Med. 2005; 30(3):210-216; Butryn M L, Phelan S, Hill J O, Wing R R. Consistent self-monitoring of weight: a key component of successful weight loss maintenance. Obesity. 2007; 15(12):3091-3096; The Technology Boom: A New Era in Obesity Management. Gilmore, Duhé, Frost, Redman. J Diabetes Sci Technol. 2014 Feb. 27; 8(3):596-608.]

In light of these statistics, it is not surprising that many people have a personal fitness goal of losing, gaining, or maintaining/monitoring weight, and/or improving their body size or shape.

Research has repeatedly shown that frequent self-monitoring, such as weighing and/or taking circumference measurements, plays an important, if not critical, role in achieving weight loss or gain, and other fitness goals.

Current methods for monitoring weight include:

Use of a weighing scale (i.e. a measuring instrument for determining the weight or mass of an object). This technique has the benefit of being inexpensive and fast, but is not able to indicate changes in body shape.

Use of a measuring tape. Whilst inexpensive, this technique is prone to user error, impractical and time consuming.

Use of Dual-energy X-ray Absorptiometry (DXA, or DEXA). This technology facilitates accurate body composition measurement, but has disadvantages of not providing body girth/circumference measurements, being expensive, and time consuming. Furthermore, it may have associated health implications. In this regard, whilst the amount of radiation used in the technology is typically extremely small, less than one-tenth the dose of a standard chest x-ray, and less than a day's exposure to natural radiation, for clinical and commercial use there have been recommendations that an individual should only be scanned twice per annum due to health implications.

Use of three dimensional (3D) body scanners and mappers, such as those provided under the trademarks Image Twin™ and mPort™. Whilst the Image Twin™ system allows for the creation of an accurate 3D avatar representation of a body, it is expensive and requires use of specialized equipment typically located in a laboratory. The mPort™ system allows for an accurate 3D avatar representation of a body to be created, and for the provision of circumference measurements. However, it is also expensive, requires use of specialized equipment at prescribed locations, and provides only graphical data for weight changes.

Use of virtual weight loss simulators, such as those provided under the trademarks Model My Diet™, Change in Seconds™, and Virtual Weight Loss Model Lite™ (software app). These systems typically allow for the generation of "before" and "after" cartoon avatar representations of a body. They are only available as executables that run on computers e.g. a desktop and provide basic estimates only using basic anthropometric data.

Use of virtual product simulators, such as that provided under the trade mark Optitex™. The Optitex™ system allows for the generation of a single cartoon avatar representation of a body. It is only available as executables that run on computers and provides basic estimates only using basic anthropometric data.

Use of photos, such as that provided under the trade mark Good Housekeeping™. The Good Housekeeping™ system is photo-based, but only allows for the simple narrowing and expanding of an uploaded photograph in the two dimensional (2D) space which is a basic type of image morphing approaches used in image manipulation/processing software (e.g. photoshop).

An investigation (published in J Diabetes Sci Technol. 2013 Jul. 1; 7(4):1057-65. Using avatars to model weight loss behaviors: participant attitudes and technology development) revealed a high level of interest in an avatar-based program, with formative work indicating promise. Given the high costs associated with in vivo exposure and practice, this investigation demonstrates the potential use of avatar-based technology as a tool for modeling weight loss behaviors.

It is against this background that the present invention has been developed.

SUMMARY OF THE INVENTION

It is an object of the present invention to overcome, or at least ameliorate, one or more of the deficiencies of the prior art mentioned above, or to provide the consumer with a useful or commercial choice.

Other objects and advantages of the present invention will become apparent from the following description, taken in connection with the accompanying drawings, wherein, by way of illustration and example, a preferred embodiment of the present invention is disclosed.

According to a broad aspect of the present invention, there is provided a device for imaging a body, the device comprising:
  a controller;
  storage storing electronic program instructions for controlling the controller;
  a display for displaying a user interface; and
  an input means;
  wherein the controller is operable, under control of the electronic program instructions, to:
    receive input via the input means, the input comprising a classification of the body and a first representation of the body;
    process the first representation given the classification of the body;
    generate a second representation of the body on the basis of the processing of the first representation; and
    display the generated second representation via the display.

According to a first broad aspect of the present invention, there is provided a device for imaging a body, the device comprising:
  a controller;
  storage storing electronic program instructions for controlling the controller;
  a display for displaying a user interface; and
  an input means;
  wherein the controller is operable, under control of the electronic program instructions, to:
    receive input via the input means, the input comprising a first representation of the body;
    display the first representation via the display;
    generate a user-specific skeleton that will appear on the display once the input is received;
    enable the user to align the body in the first representation with the user-specific skeleton;
    process the first representation when the body has been aligned with the user-specific skeleton by segmenting the first representation of the body;
    generate a second representation of the body on the basis of the processing of the first representation; and
    display the generated second representation via the display.

In an embodiment, the controller is operable, under control of the electronic program instructions, to: process the first representation of the body by segmenting the first representation of the body to obtain a plurality of silhouettes which represent in simple form, projected shadows of a substantially true three dimensional scan of the body; and generate the second representation of the body on the basis of the silhouettes.

In one embodiment, the silhouettes may include, for example, projection and human body movement fundamentals.

Advantageously the controller is also operable, under control of the electronic program instructions, to:
  instruct the user via audible sounds/words/speech to align parts of the body to the displayed user-specific skeleton, wherein the electronic program instructions are operable to control the alignment process by errors calculated using various data and/or between characteristics including shape appearance and variation features, pose features, and spatiotemporal features that are extracted from the generated skeleton and the body's real time captured image(s).

Preferably the controller is also operable, under control of the electronic program instructions, to:
  calculate on the basis of user height information submitted, image size (image height and width in pixels), and using blob analysis of binary images, projection theories and camera models, the following:
    initial estimates of intrinsic and extrinsic parameters of the capturing sensor or camera which includes camera position and orientation in each image, defined as pose P; and,
    initial estimates of joint kinematics of a skeletal model representing a skeleton of the body, defined as JK, including 3D position and 3D orientation of each joint of the skeletal model.

In this embodiment the controller is also operable, under control of the electronic program instructions, to:
  predict on the basis of the user height and weight and gender information submitted, or the user height and gender information only, an initial on-average avatar, defined as Av, which generally varies with the user's entered height, weight or other body measurements if known; and,
  rig the on-average avatar Av to a reference skeleton of size N-joints with known skeletal model and JK in a reference pose, and a bone weight/heat matrix defined as W.

Preferably the matrix W is calculated offline just once during the offline machine learning process of human shapes, then saved together with the reference skeletal model JK to be used for the prediction or generation of other avatars or human shapes that are not learned before, few purposes of W is to constrain, control and model the relationship between joints, bones and the actual 3D avatar surface or 3D topology including natural deformation occurs to human skin. The surface or 3D topology can be uniquely modeled and represented by its vertices V, edges E and faces F.

Advantageously the process of predicting the initial on-average avatar Av follows a sophisticated multivariate-based machine learning approach. Preferably the multivariate-based machine learning approach comprises an offline learning of human shape 3D geometry using unique and salient 3D features extracted from a plurality of rigged and rendered three dimensional scans of real humans (males and females) of different ages, ethnicity and in different body poses. Typically the multivariate-based machine learning approach further comprises various statistical relationships between different body measurements defined as vector $M=(m1, m2, \ldots, mL)$ with L number of different measurements wherein, in use, one or more measurements can be predicted given one or more different measurements and an on-average avatar Av can be predicted given one, or more of these measurements.

Preferably in order to deform or simply animate an avatar to a new avatar defined as Av1 of the body as represented in a new first representation, the reference or on-average avatar data (V, E, F, JK, W) and a known or an estimate of the user joint kinematics defined as JK1 of the new first representation are fed to a cost function defined as £, that optimizes and deforms Av to Av1 subject to a number of physical constraints known or learned from natural human motion wherein, in use, the new animated avatar Av1 and for simplicity assume it has same body measurements as the on-average avatar Av, can be modeled as a nonlinear function of the reference or an on-average avatar data, i.e. Av1=f(Av, W, JK, JK1). Typically an implementation of the cost function £ is derived by combining two or more weighted energy minimization functions:

a surface smoothness function utilizing e.g. Laplacian cotangent matrix which uses V, F and E; and, a bone attachment function which uses V, F, and W to ensure that the correspondence is constrained between the avatar vertices and its skeletal structure.

Preferably in order to generate the 3D representation of the actual body, the 3D avatar; one or more representation of Av1 is matched and compared using adaptive nonlinear optimization against one or more of the silhouettes or their representations. The process will tune up the initially estimates of Av1 data and measurements including M, JK until a match is achieved.

In a further embodiment, the input comprises a classification of the body, and the controller is operable, under control of the electronic program instructions, to: on the basis of the classification of the body, obtain data corresponding to the body classification; process the first representation by comparing the first representation and the obtained data; and generate the second representation of the body on the basis of the comparison.

In an embodiment, the input comprises details of the body. The details may comprise data and/or information associated with the body.

In embodiments of the invention, the data may be obtained by one more of retrieving, receiving, extracting, and identifying it, from one or more sources. In an embodiment, the obtained data comprises at least one of: a template; an earlier representation of the body, in which case the body classification may comprise an identification of the body; and an integration of, or of data of or associated with, one or more earlier representations of the body, and/or other bodies.

In an embodiment, the first representation of the body includes the classification of the body.

In an embodiment, the body is a human body, or one or more parts thereof. In such a case, the body may be classified according to anthropometry. In an embodiment, the device comprises a plurality of templates, each template having associated with it template data including a three dimensional model of a human body with standard mean anthropometry measurements. This may be referred to as an average body model The standard mean anthropometry measurements may be for one or more measurements, including measurements for sex, size (e.g. a person's clothes size), weight, height, age, and ethnic groups' variations.

In an embodiment, the body is a body of a living thing, or one or more parts thereof.

In an embodiment, the body is a body of a non-living thing, or one or more parts thereof.

The input means may comprise at least one sensor, which may be part of a sensor system or a set of sensors.

In an embodiment, the first representation comprises a visual representation of the body. In such an implementation, the at least one sensor may comprise an imaging means operable to capture the visual representation of the body. The imaging means may be a digital camera.

Individual sensors within the set of sensors may comprise: a motion sensor; an infra-red sensor; a depth sensor; a three dimensional imaging sensor; an inertial sensor; a Micro-Electromechanical (MEMS) sensor; an imaging means; an acceleration sensor; an orientation sensor; a direction sensor; and a position sensor.

In an embodiment, the first representation comprises one or more visual representations of the body. In such an embodiment, the one or more sensors, where provided, may comprise an imaging means operable to capture the one or more visual representations of the body. Furthermore, the one or more sensors may comprises an orientation sensor operable to provide orientation data for use during capture of the one or more visual representations of the body to facilitate alignment thereof to a plane for increased accuracy.

In an embodiment, the one or more visual representations of the body include at least one frontal and at least one side view photograph of the body. The photographs may comprise: standard two dimensional (2D) binary, gray or color images; depth images with or without colors and/or textures; a complete three dimensional (3D) point cloud or a number of incomplete point clouds of the body with or without colors and/or texture; and/or a three dimensional (3D) mesh of the body with or without colors and/or texture, in embodiments of the invention.

In an embodiment, the controller is further operable, under control of the electronic program instructions, to:

segment at least one foreground comprising the body of one or more visual representations of the body of the first representation;

convert the one or more segmented foregrounds of the one or more visual representations of the first representation into respective silhouettes;

use the one or more segmented foregrounds and their respective silhouettes to construct a 3D visual hull of a shape of the body, and/or extract features and/or extract measurements of key points; and use one or more of the hull, and/or features, and/or key point measurements to one or more of modify, rig, and morph a 3D model of a body (an average body model) of the selected template to create a modified subject-specific 3D model image being the second representation.

In an embodiment, in the case of depth images, point clouds and meshes, any with or without colors and/or textures, the controller is operable, under control of the electronic program instructions, to reconstruct a three dimensional subject-specific shape of the body. In an embodiment, the controller is further operable, under control of the electronic program instructions, to delete the one or more visual representations of the first representation.

The display, user interface and input means may be integrated, in a touchscreen for example. Alternatively, they may be discrete.

In an embodiment, the input comprises user instructions which are input by a user via the input means. The user instructions may comprise a command to perform an action, in which case the controller is operable, under control of the electronic program instructions, to perform the action according to the received user instructions.

The action may comprise an interaction action, and may include one or more of the following: selecting an area or portion of the generated second representation to obtain measurement details thereof.

The template may be retrieved from the storage of the device, or from storage remote from the device.

In embodiments, one or more of the first representation, the template, and the second representation may be stored in or across one or more databases.

In an embodiment, the electronic program instructions comprise software. The device may be a mobile communication device, in which case it may comprise a smartphone, notebook/tablet/desktop computer, a camera, or portable media device, having the software installed thereon. The software may be provided as a software application downloadable to the device.

Preferably, operations performed by the device occur automatically, without requiring human intervention.

According to a second broad aspect of the present invention, there is provided a method for imaging a body, the method comprising:
storing electronic program instructions for controlling a controller; and
controlling the controller via the electronic program instructions, to:
receive an input via an input means, the input comprising a first representation of the body;
display the first representation on a user display
generate a user-specific skeleton that will appear on the display once the input is received;
enable the user to align the body in the first representation with the user-specific skeleton;
process the first representation when the body has been aligned with the user-specific skeleton by segmenting the first representation of the body; and
generate a second representation of the body on the basis of the processing of the first representation.

In an embodiment, the method may further comprise communicating the generated second representation. The communicating may comprise displaying the generated second representation via a display.

In an embodiment, the method further comprises controlling the controller via the electronic program instructions, to: process the first representation of the body by segmenting the first representation of the body to obtain a plurality of silhouettes which represent in simple form, projected shadows of a substantially true three dimensional scan of the body; and generate the second representation of the body on the basis of the silhouettes. Preferably the step of enabling the user includes instructing the user via audible sounds/words/speech to align parts of the body to the displayed user-specific skeleton, wherein the electronic program instructions are operable to control the alignment process by errors calculated using and between various including shape appearance and variation features, pose features, spatiotemporal features that are extracted from the generated skeleton and the body's real time captured image(s).

Advantageously the method further comprises controlling the controller via the electronic program instructions, to:
calculate on the basis of user height information submitted, image size (image height and width in pixels), and using blob analysis of binary images, projection theories and camera models, the following:
initial estimates of intrinsic and extrinsic parameters of the capturing camera which includes camera position and orientation in each image, defined as pose P; and,
initial estimates of joint kinematics of a skeletal model representing a skeleton of the body, defined as JK, including 3D position and 3D orientation of each joint of the skeletal model.

Advantageously the method further comprises controlling the controller via the electronic program instructions, to:
calculate on the basis of user height information submitted, image size (image height and width in pixels), and using blob analysis of binary images, projection theories and camera models, the following:
initial estimates of intrinsic and extrinsic parameters of the capturing sensor or camera which includes camera position and orientation in each image, defined as pose P; and,
initial estimates of joint kinematics of a skeletal model representing a skeleton of the body, defined as JK, including 3D position and 3D orientation of each joint of the skeletal model.

Typically the method further comprises controlling the controller via the electronic program instructions, to:
predict on the basis of the user height and weight and gender information submitted, or the user height information and gender only, an initial on-average avatar, defined as Av, which varies with the user's entered height, weight or other body measurements if known;
rig the on-average avatar Av to a reference skeleton of size N-joints with known skeletal model JK in a reference pose, and a bone weight/height matrix defined as W. Preferably the matrix W is calculated offline just once during a learning process of the prediction process, then saved together with the reference skeletal model JK to be used for prediction or generation of other avatars, the purpose of W being to constrain, control and model the relationship between joints, bones and the actual 3D avatar surface represented by its vertices V, edges E and faces F.

Typically the method further comprises controlling the controller via the electronic program instructions, to:
predict on the basis of the user height and weight and gender information submitted, or the user height information and gender only, an initial on-average avatar, defined as Av, which varies with the user's entered height, weight or other body measurements if known;
rig the on-average avatar Av to a reference skeleton of size N-joints with known skeletal model and JK in a reference pose, and a bone weight/heat matrix defined as W. Preferably the matrix W is calculated offline just once during the offline machine learning process of human shapes, then saved together with the reference skeletal model JK to be used for the prediction or generation of other avatars or human shapes that are not learned before, some purposes of W are to constrain, control and model the relationship between joints, bones and the actual 3D avatar surface or 3D topology including natural deformation occurs to human skin. The surface or 3D topology can be uniquely represented by its vertices V, edges E and faces F.

Preferably the process of predicting the initial on-average avatar Av follows a sophisticated multivariate-based machine learning approach. Typically the multivariate-based machine learning approach comprises an offline learning of human shapes 3D geometry using unique and salient 3D features extracted from a plurality of rigged and rendered three dimensional scans of real humans (males and females) of different ages and poses.

Advantageously the multivariate-based machine learning approach further comprises the machine intelligence learning various statistical relationships between different body measurements defined as vector $M=(m1, m2, \ldots, mL)$ with L number of different measurements wherein, in use, one or more measurements can be predicted given one or more different measurements and an on-average avatar Av can be predicted given one, or more of these measurements.

In this embodiment, in order to deform or simply animate an avatar to a new avatar defined as Av1 of the body as represented in a new first representation, the reference or on-average avatar data (V, E, F, JK, W) and a known or an estimate of the user joint kinematics defined as JK1 of the new first representation are fed to a cost function define £, that optimizes and deforms Av to Av1 subject to a number of physical constraints known or learned from natural human motion wherein, in use, the new animated avatar Av1 and for simplicity assume it has the same body measurements as the on-average avatar Av, can be modeled as a nonlinear function of the reference or on-average avatar data, i.e. Av1=f(Av, W, JK, JK1). Typically an implementation of the cost function £ is derived by combining two or more weighted energy minimization functions:

a surface smoothness function utilizing e.g. Laplacian cotangent matrix which uses V, F and E; and, a bone attachment function which uses V, F, and W to ensure that the correspondence is constrained between the avatar vertices and its bones.

In a further embodiment and in order to generate the 3D representation of the actual body, the 3D avatar; one or more representation of Av1 is matched and compared using adaptive nonlinear optimization against one or more of the silhouettes or their representations. The process will tune up the initially estimates of Av1 data and measurements including M, JK until a match is achieved.

In a further embodiment, the input comprises a classification of the body, and the method further comprises controlling the controller via the electronic program instructions, to:

on the basis of the classification of the body, obtain data corresponding to the body classification;

process the first representation by comparing the first representation and the obtained data; and generate the second representation of the body on the basis of the comparison.

According to a third broad aspect of the present invention, there is provided a computer-readable storage medium on which is stored instructions that, when executed by a computing means, causes the computing means to perform the method according to the second broad aspect of the present invention as hereinbefore described.

According to a fourth broad aspect of the present invention, there is provided a computing means programmed to carry out the method according to the second broad aspect of the present invention as hereinbefore described.

According to a fifth broad aspect of the present invention, there is provided a data signal including at least one instruction being capable of being received and interpreted by a computing system, wherein the instruction implements the method according to the second broad aspect of the present invention as hereinbefore described.

According to a sixth broad aspect of the present invention, there is provided a system for imaging a body comprising a device according to the first broad aspect of the present invention as hereinbefore described.

According to a seventh broad aspect of the present invention, there is provided a method for achieving an objective, the method comprising using a device according to the first broad aspect of the present invention as hereinbefore described to generate and display one or more second representations of a body via the display to provide motivation for achieving the objective.

In an embodiment, the body is a human body, and the objective comprises a personal fitness goal for the human body.

BRIEF DESCRIPTION OF THE DRAWINGS

The patent or application file contains at least one drawing executed in color. Copies of this patent or patent application publication with color drawings will be provided by the Office upon request and payment of the necessary fee.

In order that the invention may be more fully understood and put into practice, preferred embodiments thereof will now be described with reference to the accompanying drawings, in which:

FIG. 2 depicts a schematic diagram of an embodiment of a device in accordance with an aspect of the present invention;

FIG. 3 depicts a simplified system diagram of the system of FIG. 1;

FIG. 4 depicts a flow chart of user completed actions of a second embodiment of a method, using a second embodiment of a system, in accordance with aspects of the present invention; and FIG. 5 depicts a process of labeling the highly likely user body in an image during use of the second embodiment of the method and system.

DESCRIPTION OF EMBODIMENTS

Figure 1:
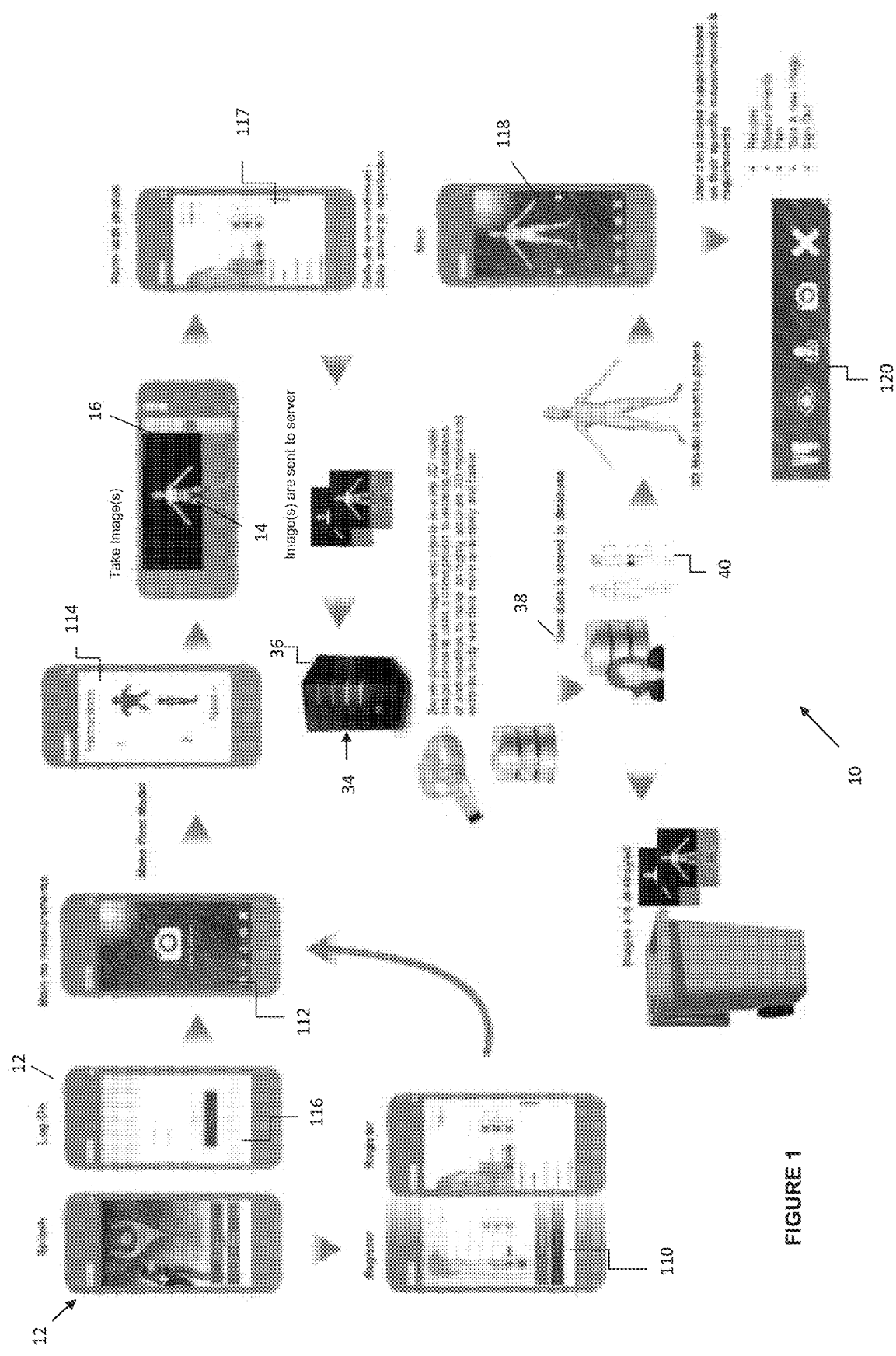
FIG. 1 depicts a flow chart of user completed actions of a first embodiment of a method, using a first embodiment of a system, in accordance with aspects of the present invention.

The present invention is not to be limited in scope by the following specific embodiments. This detailed description is intended for the purpose of exemplification only. Functionally equivalent products, compositions and methods are within the scope of the invention as described herein. Consistent with this position, those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

Further features of the present invention are more fully described in the examples herein. It is to be understood, however, that this detailed description is included solely for the purposes of exemplifying the present invention, and should not be understood in any way as a restriction on the broad description of the invention as set out hereinbefore.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

Throughout this specification relative language such as the words 'about' and 'approximately' are used. This language seeks to incorporate at least 10% variability to the specified number or range. That variability may be plus 10% or negative 10% of the particular number specified.

In the drawings, like features have been referenced with like reference numbers.

In FIG. 1, there is depicted actions performed during use of a first embodiment of a system 10 for imaging a body using a device 12 in accordance with aspects of the present invention.

In the embodiment described, the body is a body 14 of a human 16 (being a user of the system 10) desirous of achieving an objective comprising a personal fitness goal of losing, gaining, or maintaining/monitoring weight, and/or improving their body size or shape. As such, it is particularly applicable for use: by females ages 16-48 years, brides/grooms, athletes, and body builders; pre/post pregnancy; and in medical monitoring. As will be described in further detail, the system 10 is operable to provide an exact, personalised subject-specific image of the human 16 to promote and assist in the achievement of their personal fitness goal through effective and accurate monitoring of their body 14. The image provided may be referred to as an avatar.

Although the present invention will be described with particular reference to imaging a human body to promote and provide motivation for achieving a personal fitness goal, it will be appreciated that it may be used in respect of bodies of other things and for additional and/or alternative purposes or objectives.

It will be appreciated that the invention is not limited in regard to the body imaged or the purpose for which it is imaged, and in alternative embodiments, the invention may be applied to imaging bodies of additional and/or alternative things, for additional and/or alternative purposes to those described. Depending on the implementation, the body may be a body of a living thing, or one or more parts thereof, or a body of a non-living thing, or one or more parts thereof. Embodiments of the invention are particularly applicable to imaging bodies of things within which there is variation between the body of one and another, such as animals, including livestock, and food in a natural state.

The device 12 is carried a person being the user 16.

The device 12 comprises a plurality of components, subsystems and/or modules operably coupled via appropriate circuitry and connections to enable the device 12 to perform the functions and operations herein described. The device 12 comprises suitable components necessary to receive, store and execute appropriate computer instructions such as a method for imaging a body and a method for achieving an objective in accordance with embodiments of the present invention.

Particularly, and as shown in FIG. 2, the device 12 comprises computing means which in this embodiment comprises a controller 18 and storage 20 for storing electronic program instructions for controlling the controller 18, and information and/or data; a display 22 for displaying a user interface 24; and input means 26; all housed within a container or housing 28.

As will be described in further detail, the controller 18 is operable, under control of the electronic program instructions, to: receive input via the input means, the input comprising a first representation of the body 14; process the first representation; generate a second representation of the body 14 on the basis of the processing; and display the generated second representation via the display 22.

Furthermore, in the first embodiment, the input also comprises a classification of the body 14, and the controller 18 is operable, under control of the electronic program instructions, to: on the basis of the classification of the body 14, obtain data corresponding to the body classification; process the first representation by comparing the first representation and the obtained data; and generate the second representation of the body 14 on the basis of the comparison.

In embodiments of the invention, the data may be obtained by one or more of retrieving, receiving, extracting, and identifying it, from one or more sources. The one or more sources of data may reside on the storage 20, and/or elsewhere, remote from the device 12.

In the embodiment described, the obtained data is provided in the form of a template that is retrieved on the basis of the classification of the body 14, and anthropometry is used to classify the body 14.

A plurality of templates is provided, each template having associated with it template data including a three dimensional (3D) model of a human body with standard mean anthropometry measurements for items including sex and ethnic groups' variations. The templates are averaged 3D digital models with full dimensions for height and width of all body elements. In the embodiment, the device is operable to extract a sub set of these as numeric measurements that can be displayed or calculated on. As will be described in further detail, these specific data points are used to compare to the input images and allow the template to be modified to relate to the image size data.

In embodiments of the invention, the obtained data may comprise an earlier representation of the body, in which case the body classification may comprise an identification of the body.

In other embodiments, the obtained data may comprise an integration of, or of data of or associated with, one or more earlier representations of the body, and/or other bodies. Such data may have been generated via operation of the device 12 and/or been obtained from one or more other source(s), such as one or more other devices 12, or DEXA technology, for example.

The controller 18 comprises processing means in the form of a processor.

The storage 20 comprises read only memory (ROM) and random access memory (RAM).

The device 12 is capable of receiving instructions that may be held in the ROM or RAM and may be executed by the processor. The processor is operable to perform actions under control of electronic program instructions, as will be described in further detail below, including processing/executing instructions and managing the flow of data and information through the device 12.

In the embodiment, electronic program instructions for the device 12 are provided via a single software application (app) or module which may be referred to as an imaging app. In the embodiment described, the app is marketed under the trade mark MYFIZIQ™, and can be downloaded from a website (or other suitable electronic device platform) or otherwise saved to or stored on storage 20 of the device 12.

In preferred embodiments of the invention, the device 12 is a mobile communication device and comprises a smartphone such as that marketed under the trade mark IPHONE® by Apple Inc., or by other provider such as Nokia Corporation, or Samsung Group, having Android, WEBOS, Windows, or other Phone app platform. Alternatively, the device 10 may comprise other computing means such as a personal, notebook or tablet computer such as that marketed under the trade mark IPAD® or IPOD TOUCH® by Apple Inc., or by other provider such as Hewlett-Packard Company, or Dell, Inc., for example, or other suitable device.

The device 12 also includes an operating system which is capable of issuing commands and is arranged to interact with the app to cause the device 12 to carry out the respective steps, functions and/or procedures in accordance with the embodiment of the invention described herein. The operating system may be appropriate for the device 12. For example, in the case where the device 12 comprises an IPHONE® smartphone, the operating system may be iOS.

As depicted in FIG. 3, the device 12 is operable to communicate via one or more communications link(s) 30, which may variously connect to one or more remote devices 32 such as servers, personal computers, terminals, wireless or handheld computing devices, landline communication devices, or mobile communication devices such as a mobile (cell) telephone. At least one of a plurality of communications link(s) 30 may be connected to an external computing network through a telecommunications network.

In the embodiment described, the remote devices 32 include other devices 12, owned and/or operated by other persons, as well as a computing system 34 owned and operated by an administrator.

The administrator computing system 34 has the form of a server 36 in the embodiment. The server 36 may be used to execute application and/or system services such as a system and method for imaging a body and method for achieving an objective in accordance with embodiments of the present invention.

In the embodiment, the server 36 is physically located at a centrally managed administration centre. In alternative embodiments, it may be held on a cloud based platform.

Similar to the device 12, the server 36 comprises suitable components necessary to receive, store and execute appropriate electronic program instructions. The components include processing means in the form of a server processor, server storage comprising read only memory (ROM) and random access memory (RAM), one or more server input/output devices such as disc drives, and an associated server user interface. Remote communications devices 32 (including the device 12) are arranged to communicate with the server 36 via the one or more communications link(s) 30.

The server 32 is capable of receiving instructions that may be held in ROM, RAM or disc drives and may be executed by the server processor. The server processor is operable to perform actions under control of electronic program instructions, as will be described in further detail below, including processing/executing instructions and managing the flow of data and information through the computing system 34.

The server 36 includes a server operating system which is capable of issuing commands to access a plurality of databases or databanks which reside on the storage device thereof. In the embodiment, two such databases or databanks are provided, comprising: one of registered users (RU) of the system 10, which may be referred to as an RU database 38; and one of the hereinbefore described templates, including the template data, which may be referred to as a template database 40. The operating system is arranged to interact with the databases 38 and 40 and with one or more computer programs of a set/suite of server software to cause the server 36 to carry out the respective steps, functions and/or procedures in accordance with the embodiment of the invention described herein.

The app, computer programs of the server software set, and other electronic instructions or programs for the computing components of the device 12 and the server 36 can be written in any suitable language, as are well known to persons skilled in the art. For example, for operation on a device 12 comprising an IPHONE® smartphone, the imaging app may be written in the Objective-C language. In embodiments of the invention, the electronic program instructions may be provided as stand-alone application(s), as a set or plurality of applications, via a network, or added as middleware, depending on the requirements of the implementation or embodiment.

In alternative embodiments of the invention, the software may comprise one or more modules, and may be implemented in hardware. In such a case, for example, the modules may be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA) and the like.

The respective computing means can be a system of any suitable type, including: a programmable logic controller (PLC); digital signal processor (DSP); microcontroller; personal, notebook or tablet computer, or dedicated servers or networked servers.

The respective processors can be any custom made or commercially available processor, a central processing unit (CPU), a data signal processor (DSP) or an auxiliary processor among several processors associated with the computing means. In embodiments of the invention, the processing means may be a semiconductor based microprocessor (in the form of a microchip) or a macroprocessor, for example.

In embodiments of the invention, the respective storage can include any one or combination of volatile memory elements (e.g., random access memory (RAM) such as dynamic random access memory (DRAM), static random access memory (SRAM)) and non-volatile memory elements (e.g., read only memory (ROM), erasable programmable read only memory (EPROM), electronically erasable programmable read only memory (EEPROM), programmable read only memory (PROM), tape, compact disc read only memory (CD-ROM), etc.). The respective storage may incorporate electronic, magnetic, optical and/or other types of storage media. Furthermore, the respective storage can have a distributed architecture, where various components are situated remote from one another, but can be accessed by the processing means. For example, the ROM may store various instructions, programs, software, or applications to be executed by the processing means to control the operation of the device 12 and the RAM may temporarily store variables or results of the operations.

The use and operation of computers using software applications is well-known to persons skilled in the art and need not be described in any further detail herein except as is relevant to the present invention.

Furthermore, any suitable communication protocol can be used to facilitate connection and communication between any subsystems or components of the device 12, any subsystems or components of the server 36, and the device 12 and server 36 and other devices or systems, including wired and wireless, as are well known to persons skilled in the art and need not be described in any further detail herein except as is relevant to the present invention.

Where the words "store", "hold" and "save" or similar words are used in the context of the present invention, they are to be understood as including reference to the retaining or holding of data or information both permanently and/or temporarily in the storage means, device or medium for later retrieval, and momentarily or instantaneously, for example as part of a processing operation being performed.

Additionally, where the terms "system", "device", and "machine" are used in the context of the present invention, they are to be understood as including reference to any group of functionally related or interacting, interrelated, interdependent or associated components or elements that may be located in proximity to, separate from, integrated with, or discrete from, each other.

Furthermore, in embodiments of the invention, the word "determining" is understood to include receiving or accessing the relevant data or information.

In the embodiment of the invention, the display 22 for displaying the user interface 24 and the user input means 26 are integrated in a touchscreen 42. In alternative embodiments these components may be provided as discrete elements or items.

The touchscreen 42 is operable to sense or detect the presence and location of a touch within a display area of the device 12. Sensed "touchings" of the touchscreen 42 are inputted to the device 12 as commands or instructions and communicated to the controller 18. It should be appreciated that the user input means 26 is not limited to comprising a touchscreen, and in alternative embodiments of the invention any appropriate device, system or machine for receiving input, commands or instructions and providing for controlled interaction may be used, including, for example, a keypad or keyboard, a pointing device, or composite device, and systems comprising voice activation, voice and/or thought control, and/or holographic/projected imaging.

Input may also be received via at least one sensor which is part of a sensor system or a set of sensors 44 of the device 12. Individual sensors within the set of sensors 44 are operable to monitor, sense and gather or measure sensor data and/or information associated with or relating to one or more characteristics, properties and parameters of the device 12, the surrounding environment, or components, systems or devices associated therewith or coupled thereto. For example, the set of sensors 44 is operable to sense and gather sensor data relating to a state of the device 12 and/or a state of the environment surrounding the device 12. In an embodiment, the state of the device 12 comprises a position of the device 12. In an embodiment, the state of the device 12 further comprises a velocity and/or speed of the device 12. The set of sensors 44 include an inertial sensor system comprising an acceleration sensor and an orientation sensor, a direction sensor and a position sensor. Alternative embodiments of the invention may comprise additional and/or alternative sensors, including a motion sensor, an infra-red sensor, a depth sensor, a three dimensional imaging sensor, an inertial sensor, and a Micro-Electromechanical (MEMS) sensor.

The acceleration sensor is operable to measure an acceleration of the device 12 and produce an acceleration data. For example, the acceleration sensor may be an accelerometer. The orientation sensor is operable to measure a rate of change of the orientation (i.e., angular rate) of the device 12 and produce an orientation data. For example, the orientation sensor may be a gyroscope. The direction sensor is operable to determine a direction relative to the Earth's magnetic poles and produce a direction data. For example, the direction sensor may be an electronic compass. The position sensor is operable to determine a position of the device 12 and produce a position data. For example, the position sensor may be a Global Positioning System (GPS). The use and operation of such sensors is well-known to persons skilled in the art and need not be described in any further detail herein except as is relevant to the present invention.

The first representation may comprise one or more visual representations of the body 14. In the embodiment described, the first representation comprises a set of visual representations of the body 14. Accordingly, the set of sensors 44 includes imaging means in the form of a digital camera operable to capture images comprising the visual representations. The camera is integrated with the device 12 in the embodiment. The imaging means may comprise any suitable system or device facilitating the acquisition of still and/or moving images. For example, in the case where the device 12 comprises an IPHONE® smartphone, the imaging means may be an iSight™ camera. The use and operation of cameras is well-known to persons skilled in the art and need not be described in any further detail herein except as is relevant to the present invention.

The device 12 comprises operably connected/coupled components facilitating performance as described, including appropriate computer chips (integrated circuits), transceiver/receiver antennas, and software for the sensory technology being used.

One or more sensors of the set of sensors 44 may be integrated with the device 12, as may be the case where it comprises an IPHONE® smartphone. Alternatively, the device 12 may be operably coupled to one or more of the above-described set of sensors 44.

In addition to being stored on the template database 40, in the embodiment at least some of the details of the templates are stored or saved in a database 46 or databank residing on the storage 20 and accessible by the controller 18 under control of the app. These may be installed as part of the app. The controller 18 is arranged to interact with the database 46 to cause the device 12 to carry out the respective steps, functions and/or procedures in accordance with the embodiment of the invention described herein.

The details of others of the templates are stored or saved remotely, for example in one or more remote database modules residing on respective storage of one or more remote systems or devices 32, such as the template database 40 of the server 36 and accessible by the device 12 via the one or more communications link(s) 30. The controller 18 is arranged to facilitate user interaction with the one or more remote databases to make the remotely stored content available for use as required.

It will be understood that the database(s) may reside on any suitable storage device, which may encompass solid state drives, hard disc drives, optical drives or magnetic tape drives. The database(s) may reside on a single physical storage device or may be spread across multiple storage devices or modules.

The database 46 is coupled to the controller 18 and in data communication therewith in order to enable information and data to be read to and from the database 46 as is well known to persons skilled in the art. Any suitable database structure can be used, and there may be one or more than one database. In embodiments of the invention, the database 46 can be provided locally as a component of the device 12 (such as in the storage 20) or remotely such as on a remote server, as can the electronic program instructions, and any other data or information to be gathered and/or presented.

Similarly, both of the RU and template databases 38 and 40 are coupled to the server 36 and are in data communication therewith in order to enable data to be read to and from the RU and template databases 38 and 40 as is well known to persons skilled in the art. Any suitable database structure can be used. Any one or both of the RU and template databases 38 and 40 can be provided locally as a component of the server 36 (such as in the memory device) or remotely such as on a remote server, as can the server set of software. In an embodiment, several computers can be set up in this way to have a network client-server application. In the embodiment described each of the RU and template databases 38 and 40 is stored internally in the memory device of the server 36 as partitions of a single database structure. In alternative embodiments of the invention, there may be more or less databases.

Once the app is installed on the device 12, the controller 18 is operable, under control of the app, to present, via the touchscreen 42, a sequence of navigable electronic pages, screens and forms to the user 16 of the device 12 allowing for the inputting or capture of information and/or data, including data and/or information sensed via sensors of the set of sensors 44 such as images captured via the camera, instructions and commands pertinent to operation of the device 12 and the system 10.

In the embodiment described, the server software set of the server 36 comprises: a web server application, a registration and request application, an image processing application, a communication application, an invoicing/billing application, and a payment processing application.

As will be described in further detail, via the respective applications of the server software set, the server 36 is operable to perform functions including: registration and sharing of user data; extracting, converting and combining data with data received via the app; and recording all real time data passing through the app interface.

The web server application is operable to deliver content relating to the system 10 via a dedicated website, such as web pages or other electronic pages or screens, to existing or potential users of the system 10. The website is accessible via a web browser of an Internet enabled mobile communication device, such as a notebook computer or a smartphone (including the device 12 in the embodiment), operably connected to be in data communication with the system 10 via a communication network. In the embodiment described, the means of data communication is through the Internet, however, other methods, such as direct connection, may be employed in other embodiments of the invention.

The content may include general information relevant to fitness goals, advertising and promotional or public relations information delivered via an appropriate one or combination of forums or medium including, for example, services provided under the trademarks YouTube™ Facebook™ and/or Twitter™.

The web pages that may be accessed include an online registration page 110, to be completed on first use of the system 10 by a user, and request page 112. The website application is operable to enable a potential user of the system to manually register or record themselves as a user, thereby creating a personal account, and request an avatar. This is facilitated by the user completing and submitting to the server 36, via the registration and request pages 110 and 112, communications in the form of electronic registration and request forms comprising user registration and request information, respectively.

The user registration information includes details comprising information and/or data relating to the user and their body including:

1) User Identification and Contact Details: Details facilitating identification and communication with the user. These details may comprise user's full private names, username for when using the system 10, private home address, physical and/or electronic mail address to be used for forwarding correspondence, contact telephone number, authentication information (such as a password), and any other unique and/or relevant identification information as applicable. This information is used by the system 10 for communicating with the user, including correspondence related to avatars created, using the system 10, and billing.

2) User Body Details: Information and/or data relating to the body of the user. In the embodiment described, this comprises anthropometric data of the body, including sex, height, weight, clothes size (for example, small, medium, large, X-large, or XXL, to name a few), age, and ethnic group. In alternative embodiments of the invention, additional and/or alternative details relating to and/or associated with the user's body may be requested.

3) Billing and Payment Details: Details facilitating billing and receiving payment from the debtor (person) responsible for paying for use of the system 10 by the user. The billing details may comprise a physical and/or electronic mail address to be used for forwarding correspondence including, for example, billing notices for processing and payment. The payment details may comprise details of a financial account, such as a credit card account of the debtor, stored and used to purchase items associated with actions performed via the system 10, such as creating an avatar in the embodiment. Additional and/or alternative payment processing platforms can be used, including, but not limited to PayPal and Bitcoin (BTC) services, for example, in embodiments of the invention.

The request information includes the first representation. As described previously, in the embodiment the first representation comprises a set of visual representations of the body 14. Preferably, visual representations within the set of visual representations comprise different views of the body 14, and they are captured with the body 14 positioned in front of a contrasting, substantially clutter/noise free (i.e. non-busy), background. Particularly, in the embodiment described, the set of visual representations comprises, as a non-limiting example, two photographs of the body 14, being a first photograph of a front view of the body 14, and a second photograph of a side view of the body 14. To facilitate the capture and uploading of the two photographs, via the request page 112 the user 16 is able to access an image capture screen 114. The image capture screen allows for capturing and reviewing of the photographs before they are uploaded, and may comprise one or more sub-screens for guiding the user through the process. In the described embodiment, the device 12 is operable, via the controller 18 under control of the imaging app, to use data including orientation data produced via the internal gyroscope (of the orientation sensor calculating the orientation of the device 12) to ensure that the images are taken in the vertical plane for increased accuracy thereof.

In embodiments of the invention, the set of visual representations (such as the photographs) may comprise a set of images comprising one or more of: standard two dimensional (2D) including color, grey or binary (e.g. silhouettes) images; depth images with or without colors and/or textures; MRI, DEXA (DXA), X-Rays, CT-Scans, a complete three dimensional (3D) point cloud or a plurality of incomplete point clouds of the body with or without colors and/or texture; and three dimensional (3D) mesh of the body with or without colors and/or texture. The set of visual representations may comprise one or a combination of any images that is/are captured using an imaging (sensing) device which is able to sense and output data or features of any form representing a subject's shape (e.g. a human shape in the embodiment described) to a level enabling the reconstruction of the subject's physical, three dimensional (3D) surface or hull.

In embodiments of the invention, a normalization/blurring function may be provided that is operable to mask facial and/or other distinguishing features of the user in the set of visual representations, for enhanced privacy. The visual representations may be further privacy protected.

In alternative embodiments of the invention, the user registration and request information may comprise alternative or additional details, information and/or data.

All data and information collected via applications of the server software set, including the web server application and the registration application is distributed within the system 34 for use as described herein.

The RU database 38 has a plurality of RU records. Each RU record comprises a set of RU information relating to the account of an RU of the system 10, including the registration and request information as hereinbefore described, along with other information associated with the RU, such as avatars created therefor.

The server 36 has sensing means operable to sense or detect the receipt of communications comprising user registration and request information (sent via the dedicated website or other means as herein described). Upon sensing the receipt of such information, the server 36, via its processor under control of relevant applications of the server software set, including a database management module or application, is operable to generate, populate and manage records in the RU database 38, (as well as records in the template database 40) and to execute actions as described herein according to the data and information received.

A potential user can also register or record themselves as a user by providing the user registration information via email, facsimile, or other communication, which may be via a social networking service such as Facebook™ or Twitter™, for example, for automatic capture and entry into the RU database 38 by action of software of the set of server software or by a data entry operator or other employee of the administrator.

It should be noted that following successful registration, a RU may subsequently access the system 10 via an online access or "login" page 116, providing access to the system 10 once the user has entered an appropriate identification and security authorisation, such as their username and associated password.

The image processing application is operable to receive and process the submitted user body details and first representation of the body 16 to generate the second representation.

In the described embodiment, when an image, whether it is a 2D or a 3D depth image, is submitted, set defaults from registration (of the user body details) are used, which the user can update as required (as their body details change over time as they progress towards their goal, for example) via a form with photos screen 117. This advantageously reduces data entry time.

Particularly, on the basis of the sex, height, weight, with or without size, and with or without ethnic group information submitted, the image processing application is operable to classify the body 14 and determine and select a template of the plurality of templates having the 3D model closest thereto.

Once this has been done, the image processing application is operable to:

segment the foregrounds (human body) from the two photographs and convert the first representation into two respective silhouettes;

use the segmented foregrounds and their respective silhouettes to extract features and measurements of key points and/or descriptors and/or features;

use the extracted features and key point measurements to modify the 3D model of the selected template to create a modified subject-specific 3D model image (being the second representation);

associate the modified 3D model image to the user account; and delete/destroy the two photographs of the first representation.

Advantageously, in the embodiment the generated second image is specific to the subject (that is, the body being imaged), accurately representing the desired features thereof.

In embodiments of the invention, the image processing application is operable to: segment at least one foreground comprising the body of one or more visual representations of the body of the first representation; convert the one or more segmented foregrounds of the one or more visual representations of the first representation into respective silhouettes; use the one or more segmented foregrounds and their respective silhouettes to construct a hull of a shape of the body, and/or extract features and/or extract measurements of key points; and use one or more of the hull, and/or features, and/or key point measurements to one or more of modify, rig, and morph a 3D model of a body (an average body model) of the selected template to create a modified subject-specific 3D model image being the second representation.

In an embodiment, in the case of depth images, point clouds and meshes, any with or without colors and/or textures, image processing application is operable to reconstruct a three dimensional subject-specific shape of the body.

The communication application is operable to enable communication between the server 36 and devices in communication therewith. Such communication includes the communications described herein, and may be of any appropriate type including email, pop-up notifications, and SMS messages, and may be encrypted for increased security.

Communications made via the communication application may include status notifications to the user, such as notifications confirming that uploaded images have been deleted, and indicating that silhouettes are being used to create the user's 3D avatar.

Via the communication application, the modified 3D model image is communicated to the device 12 (along with an appropriate notification message) where it is displayable on a main image screen 118. The modified 3D model image generated in the embodiment is a working model, accurately reflecting the shape and measurements of the body 14 of the user, and in respect of which the user can perform one or more interactions via the user interface 24. The one or more interactions may include selecting an area or portion of the model to get exact circumference details thereof. Particularly, in the embodiment described, the user is able to "click on" or otherwise select part of the 3D model and see (via the display 22) numeric values associated with the selected part. Functionality is also provided allowing the user to rotate and zoom the 3D model via the user interface 24.

In embodiments of the invention, approximately 90 seconds may elapse between the user submitting the request information and the modified 3D model image being generated and communicated to the device 12.

In the embodiment, the model is coloured based on gender: pink for females, blue for males.

The user is able to navigate, including progressing to and returning from, the generated electronic screens and pages via execution of respective navigation interface element buttons provided thereon. Particularly, a navigation bar 120 is provided having interface element buttons via which the user can control the system 10 to perform actions including accessing support for their personal fitness goal based on their specific measurements and requirements. In the described embodiment, such support includes: accessing recipes for meals the consumption of which will assist the user to attain their personal fitness goal; measurements; plan(s), including nutritional plans and exercise programs, which may be tailored to the user; take a new image (generate a new modified 3D model image); and sign out/exit the system 10.

In embodiments of the invention, the device 12 is operable to store the generated modified 3D model image (being the second representation) and use it as the template for comparison the next time the user uses the device 12 to generate a new image of their body 14. That is to say, each time the user uses the device 12 to generate a new image of their body 14 following their initial use of the device 12, the modified 3D model image generated during their preceding use of the device 12 is used in generating the new image. Accordingly, a third representation of the body 14 is generated based on the generated second representation of the body 14, a fourth representation of the body 14 is generated based on the generated third representation of the body 14, and so on, in such embodiments.

In embodiments, support may include integration with one or more other systems, such as, for example, DEXA scan integration. In such a case, the one or more interactions that may be performed via the user interface 24 may include accessing data and/or information arising from a DEXA scan as an overlay displayed on top of the 3D model, selecting part of the 3D model and seeing (via the display 22) the DEXA scan data and/or information associated with the selected part.

The invoicing/billing application is operable to generate an invoice for each registered user comprising an amount payable according to their usage of the system 10.

The payment processing application is operable to receive payment for each invoice.

In embodiments of the invention, one or more of the described, additional and/or alternative operations performed by the system 10 occur automatically, without requiring human intervention.

The above and other features and advantages of the embodiment of the invention will now be further described with reference to the system 10 in use, with reference to the flow chart depicted in FIG. 1 of the drawings.

An interested person registers as a user of the system 10 via the registration process as hereinbefore described, resulting in them being provided with a user account.

Thereafter, the (now registered) user accesses and uses the system 10 as hereinbefore described to generate one or more modified 3D model images of their body and access the other provided support to assist them to achieve their personal fitness goal.

Over time, the user may generate a sequence of modified 3D model images of their body, showing changes therein. Via such frequent self-monitoring the user is able to assess their progress towards their personal fitness goal and, accordingly, be more likely to achieve it.

FIGS. 4 and 5 of the drawings depict actions performed during use of a second embodiment of a system 210 for imaging a body using a device 212 in accordance with aspects of the present invention. Similar or the same features of the system 210 in the second embodiment are denoted with the same reference numerals as the first embodiment.

As will be described in further detail, the second embodiment provides an ecologically valid system and method for the reconstruction of a three dimensional human body model (avatar). As will be described in further detail, the system and method utilizes one or more images of a subject given their height and/or weight (e.g. in the case of a person but without loss of generality).

In the second embodiment, the controller of the device 212 is operable, under control of the electronic program instructions, to: process the first representation of the body 14 by segmenting the first representation of the body 14 to obtain a plurality of silhouettes which represent in simple form, projected shadows of a substantially true three dimensional scan of the body 14; and generate the second representation of the body 14 on the basis of the silhouettes.

The controller is also operable, under control of the electronic program instructions, to: generate a user-specific skeleton that will appear on the display of the device 212 once the input is received; and, during the process of segmenting the first representation, enable the user to align the body 14 in the first representation with the user-specific skeleton.

Particularly, in the second embodiment, the system 210 is operable, under control of electronic program instructions of the app, to carry out the following sequential tasks (1-6) in order to generate or build a 3D avatar of the user:

Task 1: automatically segment the user in each image to get his/her binary images (silhouettes, define S) which represent in a simple form, projected shadows of the user's true 3D scan. In the second embodiment, segmentation is achieved when either or both of the following are followed:

a. the user aligns his/her body with a user-specific skeleton generated and displayed via the display 22 of the device 12 once they start capturing the first photograph of the front view of their body 14. This operation may be accompanied by visual and/or audio feedbacks delivered via the device 212 to ensure an optimal image is captured; and b. the user ensures that their face, hands, and feet are visible in the first photograph of the front view of their body and not covered. In the second photograph of the side view of their body, only the face and one or both of the feet are needed to be visible, according to the second embodiment.

Task 2: extract various types of features from the segmented silhouettes and fuse the extracted features together to form a representation (data vectors). One representation per silhouette.

Task 3: on the basis of the user height information submitted, image size (image height and width in pixels), and using blob analysis of binary images, projection theories and camera models; calculate the following:

a. initial estimates of intrinsic and extrinsic parameters of the capturing camera (which may be referred to as pose) which includes camera position and orientation in each image; define P.

b. initial estimates of joint kinematics of a skeletal model representing the user skeleton, define JK. This includes the 3D position and the 3D orientation of each joint of the skeletal model.

Task 4: on the basis of the user height and weight information submitted, or the user height information only, predict an on-average avatar (define Av), which varies with the user's entered height, weight or more body measurements if known. Av is also rigged to a reference skeleton of size N-joints and has known JK in a reference pose, and a bone weight/height matrix (define W).

In the second embodiment, the matrix W is calculated offline just once during the learning process of the prediction module, then saved in the imaging app together with a reference skeleton JK to be used for prediction or generation of other avatars. The purpose of W is to constrain, control and model the relationship between joints, bones and the actual 3D avatar surface represented by its vertices V, edges E and faces F. In other words to deform or simply animate an avatar to a new one (define Av1) of a user in an image submitted to the imaging app. The reference or average avatar data (V, E, F, JK, W) and a known or an estimate of the user joint kinematics (define JK1) of his/her submitted image are fed to a cost function that optimize and deform Av to Av1 subject to a number of physical constraints known or learned from natural human motion. Constraints may include, for example, the maximum rotation a pelvis joint can have or the 3D position and orientation of a joint with respect to another, the hierarchy of joints and which one affects the movement of the other, to name a few. In other words, the new animated avatar Av1 with same body measurement as the average avatar is a function of the reference/average data; i.e. Av1=f(Av, W, JK, JK1). In the technology of the second embodiment is derived a function that combines two weighted energy minimization functions:

a. a surface smoothness function utilizing Laplacian cotangent matrix which uses V, F and E, and b. a bone attachment function which uses (V, F, and W) to ensure that the correspondence is constrained between the avatar vertices and its bones.

The predication (for example, using Bayesian multivariate) of the initial avatar Av follows a sophisticated multivariate-based machine learning approach. In the second embodiment, this comprises machine intelligence learning (done offline) of human shapes using 3D features extracted from over 20,000 rigged and rendered three dimensional scans of real humans (males and females) of different ages and poses (thus the term ecologically valid used herein). It also comprises the machine intelligence learning of various statistical relationships between different body measurements (define vector M=(m1, m2, . . . , mL) with L number of different measurements). As an example, m1 can be the chest circumference. The technique developed, can predict one or more measurements given one or more different measurements and will predict an avatar given one, or more of these measurements. The learning process involves the use of various three dimensional shape (surface) features extracted from each real 3D scan.

It should be appreciated that the artificial intelligence and machine learning is not limited in this regard, and in alternative embodiments of the invention additional and/or alternative training, testing and validation may be used according to the body or thing intended to be imaged and the decisions to be made or classified.

Task 5:
Given a. the user's height or height and weight and gender, predict the remaining measurements in M, then generate (predict) an initial on-average avatar Av of the user. Hence Av by itself is a function of the measurements M, i.e. Av=fa(m1, m2, . . . , mL)=fa(M), b. initial estimates of the projection matrices P, c. reference pose joint kinematics JK of Av and its bone matrix W, d. segmented silhouettes define S of the first representation Problem:

Given the above, find the avatar Av1 and its accurate measurements define M1 of the user?

Solution:

a—Initialize M1 with M b—As the user have different body pose from the reference one, we assume his/her joint kinematics are JK1 and we initialize them with the reference offline pose JK c—Initialize P1 with P, where P1 will be the accurate camera parameters d—Form the function Av1=f(V, F, E, M1, JK1, W)

Adaptive and iterative constrained convex optimization techniques are then used to minimize a cost function that compares or match the user's silhouettes S, representations or salient features extracted from the user's silhouettes and the projected silhouettes of the avatar Av1, i.e. S verses silhouettes of Av1.

Silhouettes of Av1 are evaluated using the projection of Av1=P1(Av1) followed by image morphing processes (including, for example, smoothing, edge detection, erosion, dilation, hole filling, removal of isolated pixels and small blobs using connected component analysis). The developed optimization process of the imaging technology adaptively and automatically tunes (i) the initially predicated measurements M to reach the new body-specific values M1, (ii) the initially estimated projection matrices P to the reach the new actual ones P1, and (iii) the initially estimated joint kinematics JK to the new and actual values JK1 of body in the real 3D word. All in a single iterative and constrained manner until it reaches a local minima and the user's silhouettes (or their features or representation) matched the avatar's Av1 projected silhouettes. Constraints include, for example, the maximum and minimum values a person's hip, waist, etc. can be realistically, the maximum and minimum the position and orientation of a certain joint among the JK can have; or the maximum rotation angle and translation (offset) a camera can have.

Unlike prior art systems, the system and method of the second embodiment does not require a discrete principal component analysis (PCA)-based LOOKUP table to find the closest silhouette or avatar that matches a user avatar or silhouettes. Developed model-based multivariate-based machine learning approach represent each of the learnt 3D scan as a point in the high dimensional hyperspace (such as Remainen, Grassmannian manifolds, or Lie group). It does not require any manual adjustment nor a reference object in the captured images. Furthermore, the overall optimization process is fully automatic and enables the generation of an accurate user-specific avatar, automatic estimation of the user pose in each image and the automatic estimation of camera intrinsic and extrinsic parameters.

Task 6: to match the silhouettes in 5, various features and representations are tested and the optimal ones selected. For example, feature based on: Direct Cosine Transform DCT, corners/edges, Histogram of Oriented Gradients (HOG), Speeded Up Robust Features (SURF), Scale-Invariant Feature Transform (SIFT), and Curvlet Features to name a few.

Electronic program instructions for the system 10 of the second embodiment comprise a plurality of software modules, including a registration module (front app), an image capturing module, image inspection and pre-processing modules, foreground (user's silhouette) segmentation module, and an avatar and silhouettes matching module.

Registration Module (Front App)

The registration module (front app) of the second embodiment operates similarly to the website application of the first embodiment, and facilitates the user entering information and/or data relating to their body. In the second embodiment, this may include the user's height and weight, or their height only. It may also be operable to receive an indication from the user as to whether she/he wishes to contribute their data to a testing phase or learning phase of the system 10, which may determine the extent to which received images, etc, are blurred or encrypted, for example.

In the second embodiment, user data is stored in the cloud over SSL and private data are encrypted.

Image Capturing Module

The image capturing module is operable to provide options to the user to input image(s) to the system, including classic options and smart options.

Via the classic options, the user captures one or multiple images using their own digital cameras or any type of images (such as those herein described), and is guided to upload images using a personal computer, a laptop, an ipad, a tablet or similar device.

Via the smart options (applicable when using smart phones, personal computers, laptops, a tablet or similar device), the user captures their images using a smart phone, a camera connected to or built-in laptop, a personal computer, or any device that integrates a capturing device (e.g. a camera) and is able to run programs, scripts, apps or similar.

The image capturing module is operable to provide visual and audio aids to guide the user to capture optimal image(s), depending on whether the user is capturing the images by herself/himself or another person is capturing the images.

Without loss of generality, visual aids such as a real time human tracker(s) and/or a human face tracker(s) are triggered then initiated during the capturing process to help a $3^{rd}$ person to capture the best optimal images.

In this regard, the image capturing module comprises adaptive kernel-based trackers that learn how to detect and track the human face using the fusion of unique key points and distinctive facial features, and spatiotemporal features in either color or grayscale images. Eye, nose, ears and mouth detectors and trackers are indirect sub-modalities that are also covered within the main face tracker. Developed trackers use deterministic, single and multivariate probabilistic models.

Human trackers follows the same technicality as face trackers, but with distinctive human shape and motion features stated herein.

As hereinbefore described, the image capturing module is operable to generate a unique subject (user)-specific human skeleton to guide the user to capture optimal images. For this purpose advanced artificial intelligence and machine learning techniques involving multivariate data analysis are used to learn a model responsible for the generation of the three dimensional positions of the skeleton joints given the subject height and weight or just the weight. In the second embodiment, the learning process is constrained by ground truth (real) anatomical data belong to 3D scans of over 20,000 real human subjects, hence the term ecologically valid. Convex optimization and fitting processes, geometry contraction are also developed to skin, rig the 3D scans to their curve skeleton, anatomical skeletons and obtain the correspondence between each of two of them.

It should be appreciated that the artificial intelligence and machine learning is not limited in this regard, and in alternative embodiments of the invention additional and/or alternative models may be learned and skeletons generated according to the body or thing intended to be imaged. The constraints of the learning process may comprise more or less data, and additional and/or alternative type(s) of data than that of the second embodiment, as appropriate to the implementation of the invention.

During the capturing process, the above approach implemented by the system 210 generates and shows (on touchscreen 142 of the device 212) a real-time on-screen human skeleton comprising a number of bones and joints. The user is then asked via audible sounds/words/speech (generated by operation of the system 210 and output via the device 212) to align their body parts such as chest, arms, legs and head, to the bones of the on-screen human skeleton. The image capturing module is operable to control the alignment process by errors calculated between characteristics and various data including shape appearance and variation features, pose features, spatiotemporal (or optical flow features, or other motion data vectors, to name a few) that are extracted from the generated skeleton and the user's real time captured image(s). Output from sensors of the set of sensors of the device 212, such as three dimensional orientation gyroscopes angles captured by gyroscope thereof, are also utilized in this module to further guarantee optimal straight image captures.

Error categories and types between the skeleton pose and the user pose in the images are then fed or inputted to a feedback module to guide the user to take the optimal images (pictures).

The alignment process and the visual and audio feedback module work simultaneously until an acceptable alignment between the user image and the skeleton is achieved, as depicted in FIG. 4 of the drawings.

Image Inspection and Pre-Processing Modules

The image inspection and pre-processing modules are operable to thoroughly inspect the captured images for one or more problems, and preferably any problems whatsoever, impacting on the reconstruction of an accurate human avatar. Such problems may include, but are not limited to: users' errors, errors due images qualities, errors due to intrinsic and extrinsic noise, foreign subjects, the presence of multiple subjects and distortion due to camera lenses. This is done in two levels in the second embodiment:

a. a first level of inspection is at the app level where (i) the app is operable to check for the presence of the subject of interest (comprising a human user, as an example of a subject, in the second embodiment). For this task, a simplified but efficient face, and human detectors and trackers have been developed and which are operable to inspect, and accept or reject the images on basis of the inspection. (ii) The app also uses built in gyroscope data of the device 212 to guide the user to capture optimal images and is operable to accept or reject images according to a set of pre-defined pose thresholds. (iii) The app is also operable to check details of the images, including, for example, format, size (including dimensions in pixels and storage required) to determine if prescribed criteria are satisfied and they are acceptable. If accepted, the app is operable to then reduce the size of the images while maintain the quality to greater or equal to 99% of the original accepted quality. In any of these steps audio and visual feedback may be generated and presented to guide the user (as hereinbefore described).

b. A second level of inspection is an in-depth one which occurs within an advanced image pre-processing (AIPP) module running in the cloud and which operates as follows.

i. the AIPP filters the captured images using a Gaussian kernel of a variable size and variance to minimize noise in images and prepare the images for the upcoming process segmentation.

ii. the AIPP also builds statistical tests based on probability and joint probability functions estimated using pixel color values or their intensities, and their image positions. It then corrects for illumination and lighting related variations or shadows. The statistical tests will then decide whether to accept or reject an image based on a pre-defined threshold identified through off-line testing of a large database of images.

iii. the AIPP inspects and will reject images that have multiple faces, flipped irregularly or distorted images, images with multiple people/person complete/incomplete, images that have any foreign subject or backgrounds that have characteristics which interfere with the main subject (user), images that have incomplete capture of a user body except for cases where a user has indicated that he/she is an amputee and provided additional data or cases where two more images are used (in the case of two images, a full capture of the user frontal view must be presented). For this purpose/task machine learning approaches are used and driven by variety of fused, multimodality salient image features, descriptors and key points extracted from a large data base of images including videos containing one or more people or none. Features, descriptors and key points belong to the human skin, face, nose, mouth, ears, arms, upper body, lower body, legs, foot (to name a few), are also used for the training, testing and validation of the said machine learning in this inspection module.

It should be appreciated that the artificial intelligence and machine learning is not limited in this regard, and in alternative embodiments of the invention additional and/or alternative training, testing and validation may be used according to the body or thing intended to be imaged and the decisions to be made.

Foreground (User's Silhouette) Segmentation Module

Most prior art work done on foreground-background segmentations from a single image assumes a known or semi-known background characteristic(s), such as the chroma key screens used in TV shows. Others seek users to manually digitize their images or identify their body in an image or images. However, the outlines of the user's body in an image or distinctive features belonging to the user or the background (if known, determined/entered or can be estimated), provide strong constraints on the segmentation of an accurate silhouette of the body shape.

The inventors have developed an iterative approach based on optimization by "graph-cut" fundamentals to segment the silhouettes of a person in an image, used in a fully automatic manner. The inventive approach extends the principals used in standard graph-cuts such as max-flow min-cut theorem, Bayes Matting (including tri-maps) and probabilistic color models in a number of aspects, most importantly, in the second embodiment, it is fully automatic and is robust when foreground and background color distributions are not well separated since the inventors probability models include not only pixels intensities but their positions and their relevance/connection (adherence) to the structure of a human shape (graph). Steps of the developed approach, which the system 210 of the second embodiment is operable to perform, can be summarized as follows.

The approach requires some or all of the following inputs in order to segment the user silhouette from an image. The invention identifies them automatically i. A bounding box or a region, or a blob in the image which contains the user body. This is used for what is known as "hard" segmentation graph-cut scenario.

ii. Foreground regions or features in the image that are definitely, highly likely, likely/probably a user body.

iii. Background regions or features in the image that are definitely, highly likely, likely/probably a not the user body.

In other words, each pixel in the image is given a probability value that tells the likelihood it belongs to the foreground or the background.

Since the user is asked to align his/her body with the on-screen skeleton mentioned earlier, thus:

iv. The bounding box (region) encompassing the skeleton, strictly defines the one required in (i) above. However in order to cater for uncertainty errors, an uncertainty factor, of 5% in the second embodiment, is added to the region positions, i.e. it is increased by 5% v. Image pixels along (overlaps or co-registered with) the skeleton bones are definitely or highly likely part of the person's body and this satisfies (ii) above. The system 210 is operable to further enhance and expand these "definite" body parts image regions by dilating those overlapped image-skeleton regions by kernels of variable sizes. The sizes may be proportional to the body part. For example the area along the back bone is dilated by a kernel of a larger size than the one of an arm, as depicted in FIG. 2 of the drawings.

vi. Pixels outside the bounding box are highly likely belong to the background and this satisfies (iii) above.

vii. Pixels within the bounding box that are not marked as either foreground or background are given equal probabilities until it is checked by another approach, described below.

This sub-module is operable to further strengthen the segmentation of accurate silhouettes. A Bayesian-based skin color detector was also learned and developed which identifies pixels in image that are likely have a skin color. This is operable to allow for the detection and segmentation (not identification) of the user's face, hands, and feet (in the worst case scenario where the rest of the body is covered), and other unwanted skin-like subjects. The system 210 is operable to then use connected component analysis and fitting, curvature analysis to analyse those segmented skin-blobs and create semi-skeleton links. Adjacency data (matrix) is then reconstructed and analyzed to remove blobs that are not part of a human skeleton links (bones-like). Remaining blobs are then classified as highly likely part of the user body.

A learned face detector is then used to further refine the aforementioned approaches by detecting the user face. Once the face or a face profile is detected, a pre-defined mask is then applied to crop the face region that has the person skin tone only, meaning eyes, eye brows, and mouth are detected and removed. A back-projection algorithm based on color histograms of the cropped face mask is then applied to identify pixels in the image that have the same statistics as the ones of the face mask. The output of this submodule in the second embodiment comprises blobs that have the user specific skin tone which will further add to and refine the classification of pixels and regions needed for the described iterative graph-cut approach.

Finally pixels' colors, their position, and their classifications are fed to proposed iterative graph-cut to segment the user silhouette. This is followed by a number of image processing and morphing processes which the system 210 is operable to perform, such as image and edge smoothing, hole and missing data filling, and removal of small isolated blobs.

Avatar and Silhouettes Matching Module.

The avatar and silhouettes matching module is operable to perform the avatar and silhouettes matching process in accordance with Tasks 4, 5, and 6 as herein described.

In summary, the second embodiment of the invention uses a 3D articulated model (human model/avatar rigged to a skeleton). A graph match type of foreground segmentation (silhouette) is used, constrained by image data overlapping an on-screen human skeleton. Skin, face, nose, mouth, and ear detectors and tracker are used to improve/constrain this further. A smart mask is used to get a user-specific skin tone. Back projection techniques are then used to classify user unique skin blobs and reject those that don't match or don't comply with determined connectivity analysis relating to how human body parts are connected and their relevance to one another. Also used is principal geodesic analysis (PGA), and general manifolds. In geometric data analysis and statistical shape analysis, principal geodesic analysis is a generalization of principal component analysis to a non-Euclidean, non-linear setting of manifolds suitable for use with shape descriptors and representations.

It will be appreciated that the described embodiments of the invention provide several advantages.

A primary benefit of an embodiment of the invention is that it provides for the user to have factual data that is the result of their weight loss/weight gain/weight maintenance efforts, and in this respect the embodiment of the invention may be seen to function as an educational tool. As data from users is gathered, embodiments of the invention may comprise one or more predictive algorithms operable to estimate potential health benefits for users. In this regard, as herein described, in embodiments of the invention the retrieved data may comprise an integration of, or of data of or associated with, one or more earlier representations of the body, and/or other bodies, and the data may have been generated via operation of the device 12 and/or been obtained from one or more other source(s), such as one or more other devices 12, or DEXA technology, for example. On the basis of such data, which may include caloric intake and movement of the user over a period of time, via the one or more predictive algorithms the device 12 is operable to generate and display one or more predictive avatars showing what the body 14 of the user is likely to look like if such a regime is maintained.

Devices 12 of embodiments of the invention may be operable to seek out, locate, and establish communication with such other source(s).

Embodiments of the invention provide for the generation of an exact, personalised avatar to promote weight loss (and/or other personal fitness goal(s)) through effective and accurate monitoring. The avatar may be created instantly, and via a non-invasive procedure. Storage of generated avatars and associated data allows for time lapse comparisons to be made, allowing for precise monitoring of body changes.

The embodiment of the invention may be used to provide feedback to promote further health changes. Via the system, a sequence of avatars may be generated showing changes in the body of a user over time. The sequence of avatars creates a historical case study of the users efforts. The user can quantitatively see results (vs using photographs which have observer bias).

By using a small range of standard templates and silhouettes, errors arising from poor images are reduced, as are the processing requirements. This results in improved user experience by making the process faster and at a lower cost.

Furthermore, features of the segmented foregrounds and silhouettes allow users' submitted images to be stored with no personal photographic images data. In the described embodiment, the photographic images of the user are destroyed, thereby providing enhanced protection to privacy of the user.

It will be appreciated by those skilled in the art that variations and modifications to the invention described herein will be apparent without departing from the spirit and scope thereof. The variations and modifications as would be apparent to persons skilled in the art are deemed to fall within the broad scope and ambit of the invention as herein set forth.

The invention claimed is:

1. A device for imaging a body of a user, the device comprising:
   a controller;
   storage storing electronic program instructions for controlling the controller;
   a display for displaying a user interface; and
   an image capturing device configured to capture visual images;
   wherein the controller is operable, under control of the electronic program instructions, to:
   receive input at least in part via the image capturing device, the input comprising a first representation of the body, and the first representation comprising one or more visual representations of the body;
   display the first representation via the display;
   generate, using (i) a model of skeleton joint positions, and (ii) at least a weight of the user, a user-specific skeleton that will appear on the display once the input is received;
   enable the user to align the body in the first representation with the user-specific skeleton, at least in part by (i) displaying the user-specific skeleton along with one or more real time captured images of the body and (ii) instructing the user to move in such a manner that the displayed body is aligned to the displayed user-specific skeleton;
   process the first representation, when the displayed body has been aligned with the displayed user-specific skeleton, by segmenting the first representation of the body to obtain a plurality of silhouettes which correspond to projected shadows of a substantially true three dimensional scan of the body;
   generate a second representation of the body on the basis of the plurality of silhouettes; and
   display the generated second representation via the display.

2. A device according to claim 1, wherein the controller is operable, under control of the electronic program instructions, to:
   generate the second representation of the body on the basis of the plurality of silhouettes and thousands of known human shapes learned offline using intelligent machine learning techniques.

3. A device according to claim 1, wherein the controller is also operable, under control of the electronic program instructions, to:
instruct the user via audible sounds, words, or speech to align parts of the displayed body to the displayed user-specific skeleton, wherein the electronic program instructions are operable to control the alignment process by errors calculated between characteristics including shape features, pose features, and spatiotemporal features that are extracted from the generated skeleton and the one or more real time captured images of the body.

4. A device according to claim 3, wherein the controller is also operable, under control of the electronic program instructions, to:
calculate, on the basis of user height information submitted and image height and width in pixels, and using blob analysis of binary images, projection theories and camera models, the following:
initial estimates of intrinsic and extrinsic parameters of a capturing camera which includes camera position and orientation in each image, defined as pose P; and
initial estimates of joint kinematics of a skeletal model representing a skeleton of the body, defined as JK, including 3D position and 3D orientation of each joint of the skeletal model.

5. A device according to claim 3, wherein the controller is also operable, under control of the electronic program instructions, to:
predict, on the basis of user height and weight information submitted, or the user height information only, an initial on-average avatar, defined as Av, which varies with the user's entered height, weight or other body measurements if known; and
rig the on-average avatar Av to a reference skeleton of size N-joints with known skeletal model JK in a reference pose, and a bone weight/height matrix defined as W.

6. A device according to claim 5, wherein the matrix W is calculated offline just once during a learning process of the prediction process, then saved together with the reference skeletal model JK to be used for prediction or generation of other avatars, wherein W is used to constrain, control and model the relationship between joints, bones and the actual 3D avatar surface represented by its vertices V, edges E and faces F.

7. A device according to claim 6, wherein the process of predicting the initial on-average avatar Av follows a multivariate-based machine learning approach.

8. A device according to claim 1, wherein the input further comprises a classification of the body, and the controller is operable, under control of the electronic program instructions, to:
on the basis of the classification of the body, obtain data corresponding to the body classification;
process the first representation further by comparing the first representation and the obtained data; and
generate the second representation of the body further on the basis of the comparison.

9. A device according to claim 8, wherein the obtained data comprises at least one of: a template; an earlier representation of the body; and an integration of, or an integration of data associated with, one or more earlier representations of one or both of (i) the body, and (ii) other bodies.

10. A device according to claim 1, wherein the input is in part received via one or more of: a motion sensor; an infra-red sensor; a depth sensor; a three dimensional imaging sensor; an inertial sensor; a Micro-Electromechanical (MEMS) sensor; an acceleration sensor; an orientation sensor; a direction sensor; and a position sensor.

11. A device according to claim 10, the input is in part received via an orientation sensor operable to provide orientation data for use during capture of the one or more visual representations of the body to facilitate alignment thereof to a plane for increased accuracy.

12. A device according to claim 11, wherein the one or more visual representations of the body include at least one photograph of a front view of the body and at least one photograph of a side view of the body, and wherein the photographs comprise at least one of:
standard two dimensional (2D) binary, gray or color images;
depth images with or without one or both of colors and texture;
a complete three dimensional (3D) point cloud or a number of incomplete point clouds of the body with or without one or both of colors and texture; or
a three dimensional (3D) mesh of the body with or without one or both of colors and texture.

13. A device according to claim 12, wherein the controller is further operable, under control of the electronic program instructions, to:
instruct the user via audible sounds, words, or speech to align parts of the body to the displayed user-specific skeleton, wherein the electronic program instructions are operable to control the alignment process by errors calculated between characteristics and various data including shape features, pose features, and spatiotemporal features that are extracted from the generated skeleton and the one or more real time captured images of the body;
segment one or more foreground regions or features of the one or more visual representations of the body that are definitely, highly likely, or likely/probably the body;
convert the one or more segmented foreground regions or features of the one or more visual representations into respective ones of the plurality of silhouettes;
use the one or more segmented foreground regions or features and their respective silhouettes to one or more of (i) construct a hull of a shape of the body, (ii) extract features, or (iii) extract measurements of key points; and
use one or more of the hull, features, or key point measurements to one or more of modify, rig, and morph a 3D model of an average body of the selected template to create a modified subject-specific 3D model image being the second representation.

14. A device according to claim 13, wherein in the case of depth images, point clouds and meshes, any of which are with or without one or both of colors and textures, the controller is operable, under control of the electronic program instructions, to reconstruct a three dimensional subject-specific shape of the body.

15. A method for imaging a body of a user, the method comprising:
storing electronic program instructions for controlling a controller; and
controlling the controller via the electronic program instructions, to:
receive an input via an image capturing device configured to capture visual images, the input comprising a first representation of the body, and the first representation comprising one or more visual representations of the body;
display the first representation on a user display;

generate, using (i) a model of skeleton joint positions, and (ii) at least a weight of the user, a user-specific skeleton that will appear on the display once the input is received;

enable the user to align the body in the first representation with the user-specific skeleton, at least in part by (i) displaying the user-specific skeleton along with one or more real time captured images of the body and (ii) instructing the user to move in such a manner that the displayed body is aligned to the displayed user-specific skeleton;

process the first representation, when the displayed body has been aligned with the displayed user-specific skeleton, by segmenting the first representation of the body to obtain a plurality of silhouettes which correspond to projected shadows of a substantially true three dimensional scan of the body;

generate a second representation of the body on the basis of the plurality of silhouettes; and display the generated second representation.

16. A method according to claim 15, wherein enabling the user to align the body with the user-specific skeleton includes instructing the user via audible sounds, words, or speech to align parts of the body to the displayed user-specific skeleton, and wherein the electronic program instructions are operable to control the alignment process by errors calculated between characteristics including shape features, pose features, and spatiotemporal features that are extracted from the generated skeleton and the one or more real time captured-images of the body.

17. A method according to claim 16, further comprising controlling the controller via the electronic program instructions, to:

calculate, on the basis of user height information submitted and image height and width in pixels, and using blob analysis of binary images, projection theories and camera models, the following:
initial estimates of intrinsic and extrinsic parameters of the capturing camera which includes camera position and orientation in each image, defined as pose P; and
initial estimates of joint kinematics of a skeletal model representing a skeleton of the body, defined as JK, including 3D position and 3D orientation of each joint of the skeletal model.

18. A method according to claim 17, further comprising controlling the controller via the electronic program instructions, to:

predict, on the basis of user height and weight information submitted, or the user height information only, an initial on-average avatar, defined as Av, which varies with the user's entered height, weight or other body measurements if known; and rig the on-average avatar Av to a reference skeleton of size N-joints with known skeletal model JK in a reference pose, and a bone weight/height matrix defined as W.

19. A method according to claim 18, wherein the matrix W is calculated offline just once during a learning process of the prediction process, then saved together with the reference skeletal model JK to be used for prediction or generation of other avatars, wherein W is used to constrain, control and model the relationship between joints, bones and the actual 3D avatar surface represented by its vertices V, edges E and faces F.

20. A method according to claim 19, wherein the process of predicting the initial on-average avatar Av follows a multivariate-based machine learning approach.

21. A method according to claim 20, wherein the multivariate-based machine learning approach comprises offline machine intelligence learning of human shapes using 3D features extracted from a plurality of rigged and rendered three dimensional scans of real humans of different ages and poses.

22. A method according to claim 21, wherein the multivariate-based machine learning approach further comprises machine intelligence learning of various statistical relationships between different body measurements defined as vector M=(m1, m2, . . . , mL) with L number of different measurements wherein, in use, one or more measurements can be predicted given one or more different measurements and an on-average avatar Av can be predicted given one or more of these measurements.

23. A method according to claim 22, wherein in order to deform or simply animate an avatar to a new avatar defined as Av1 of the body as represented in a new first representation, the reference or on-average avatar data (V, E, F, JK, W) and a known, or an estimate of, user joint kinematics defined as JK1 of the new first representation are fed to a cost function that optimizes and deforms Av to Av1 subject to a number of physical constraints known or learned from natural human motion wherein, in use, the new animated avatar Av1 with same body measurement as the on-average avatar Av is a function of the reference or on-average data, such that Av1=f(Av, W, JK, JK1).

24. A method according to claim 23, wherein a function is derived that combines two weighted energy minimization functions:
a surface smoothness function utilizing a Laplacian cotangent matrix which uses V, F and E; and,
a bone attachment function which uses V, F and W to ensure that correspondence is constrained between the avatar vertices and its skeletal structure.

25. A method according to claim 15, wherein the input further comprises a classification of the body, and further comprising controlling the controller via the electronic program instructions, to:
on the basis of the classification of the body, obtain data corresponding to the body classification;
process the first representation further by comparing the first representation and the obtained data; and
generate the second representation of the body further on the basis of the comparison.

26. A non-transitory computer readable storage medium on which is stored instructions that, when executed by one or more processors causes the one or more processors to:
receive an input via an image capturing device configured to capture visual images, the input comprising a first representation of the body, and the first representation comprising one or more visual representation of the body;
display the first representation on a user display;
generate, using (i) a model of skeleton joint positions, and (ii) at least a weight of the user, a user-specific skeleton that will appear on the display once the input is received;
enable the user to align the body in the first representation with the user-specific skeleton, at least in part by (i) displaying the user-specific skeleton along with one or more real time captured images of the body and (ii) instructing the user to move in such a manner that the displayed body is aligned to the displayed user-specific skeleton;
process the first representation, when the displayed body has been aligned with the displayed user-specific skeleton, by segmenting the first representation of the body to obtain a plurality if silhouettes which correspond to projected shadow of a substantially true three dimensional scan of the body;

generate a second representation of the body of the basis of the plurality of silhouettes; and display the generated second representation.

* * * * *

UNITED STATES PATENT AND TRADEMARK OFFICE
CERTIFICATE OF CORRECTION

PATENT NO. : 9,949,697 B2
APPLICATION NO. : 15/612441
DATED : April 24, 2018
INVENTOR(S) : Katherine Iscoe et al.

Page 1 of 1

It is certified that error appears in the above-identified patent and that said Letters Patent is hereby corrected as shown below:

In the Claims

At Column 35, Line 5, Claim 26, "body of the" should be -- body on the --.

Signed and Sealed this
Nineteenth Day of March, 2019

Andrei Iancu
*Director of the United States Patent and Trademark Office*